(12) United States Patent
Landry et al.

(10) Patent No.: US 6,932,767 B2
(45) Date of Patent: Aug. 23, 2005

(54) DIAGNOSTIC MEDICAL ULTRASOUND SYSTEM HAVING A PIPES AND FILTERS ARCHITECTURE

(75) Inventors: Peter B. Landry, Lynnwood, WA (US); Christian H. Marney, Issaquah, WA (US); Suresh B. Krishnamurthy, Issaquah, WA (US); David A. Waataja, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 47 days.

(21) Appl. No.: 10/393,062

(22) Filed: Mar. 20, 2003

(65) Prior Publication Data

US 2004/0186379 A1 Sep. 23, 2004

(51) Int. Cl.$^7$ ................................................. A61B 8/00
(52) U.S. Cl. ..................................................... 600/437
(58) Field of Search ................................. 600/437, 443, 600/447; 128/916; 702/16; 710/58–61, 264; 711/100; 712/16, 201

(56) References Cited

U.S. PATENT DOCUMENTS

| | | | | |
|---|---|---|---|---|
| 5,795,297 A | * | 8/1998 | Daigle ......................... | 600/447 |
| 6,210,327 B1 | * | 4/2001 | Brackett et al. ............ | 600/437 |
| 6,253,245 B1 | | 6/2001 | Helbig ........................ | 709/232 |
| 6,306,089 B1 | * | 10/2001 | Coleman et al. ............ | 600/437 |
| 6,368,285 B1 | | 4/2002 | Osadchy et al. ............ | 600/508 |
| 6,379,306 B1 | * | 4/2002 | Washburn et al. .......... | 600/454 |
| 6,442,223 B1 | | 8/2002 | Dreps et al. ................ | 375/354 |
| 6,526,163 B1 | * | 2/2003 | Halmann et al. ........... | 382/128 |
| 6,547,730 B1 | * | 4/2003 | Lin et al. .................... | 600/437 |
| 6,633,833 B2 | * | 10/2003 | Sharma et al. .............. | 702/188 |
| 6,701,341 B1 | * | 3/2004 | Wu et al. .................... | 709/200 |
| 6,783,493 B2 | * | 8/2004 | Chiang et al. .............. | 600/437 |
| 2002/0052866 A1 | * | 5/2002 | Wortmann et al. ............. | 707/1 |
| 2002/0099571 A1 | * | 7/2002 | Waku et al. .................. | 705/2 |

OTHER PUBLICATIONS

Linetsky, Michael, "Programming Microsoft DirectShow", *Multimedia Programming* Manual, 2002, Contents pp. iii–viii, Introduction pp. xiii–xvi.

Buschmann, F.; Meunier, R.; Rohnert, H.; Sommerlad, P.; Stal, M., *Pattern–Oriented Software Architecture—A System Of Patterns*, "Pipes and Filters", 1996, pp. 53–70.

* cited by examiner

*Primary Examiner*—Francis J. Jaworski

(57) ABSTRACT

A diagnostic medical ultrasound system is disclosed. The system obtains data representative of an ultrasonic echo, processes that data in a sequential architecture, and transmits the result to an output. Further, the ultrasound system provides an interface for non-sequentially architectured applications to interact within the sequential architecture of the present invention.

30 Claims, 15 Drawing Sheets

Fig. 1-A
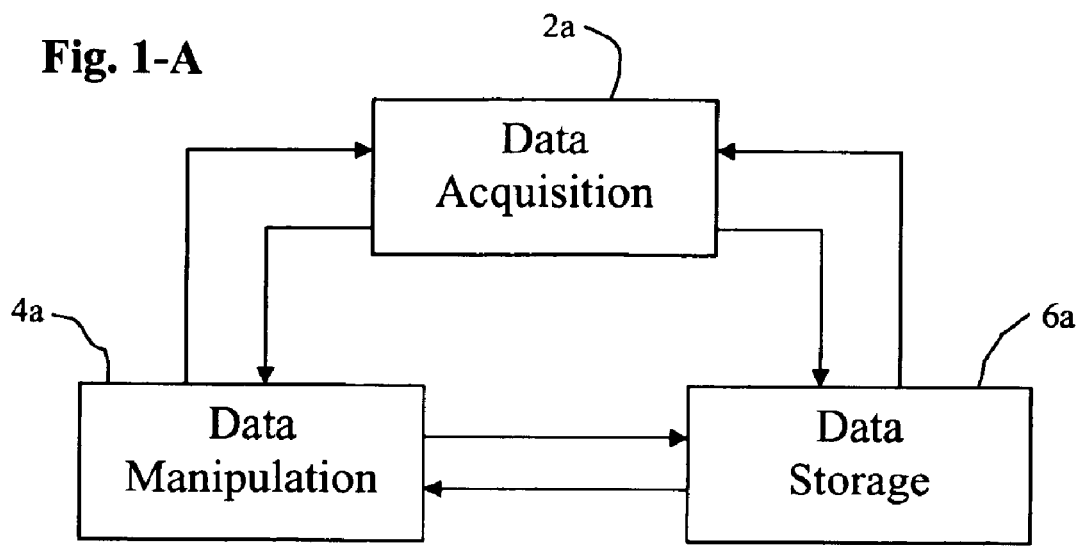
Monolithic Ultrasound Streaming Application
PRIOR ART
Fig. 1-B
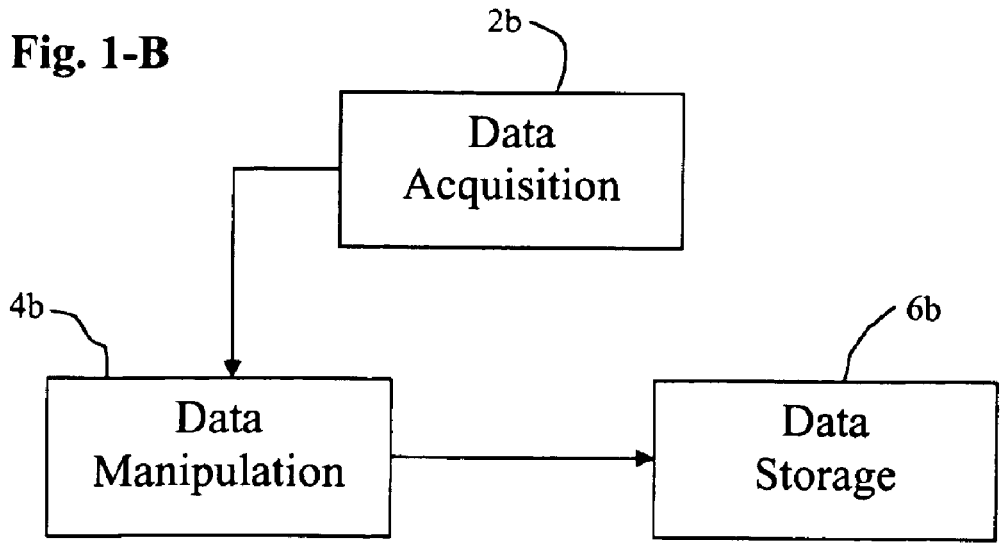
Modular Ultrasound Streaming Application
PRIOR ART Pipes and Filters Framework Based
Ultrasound Streaming Application

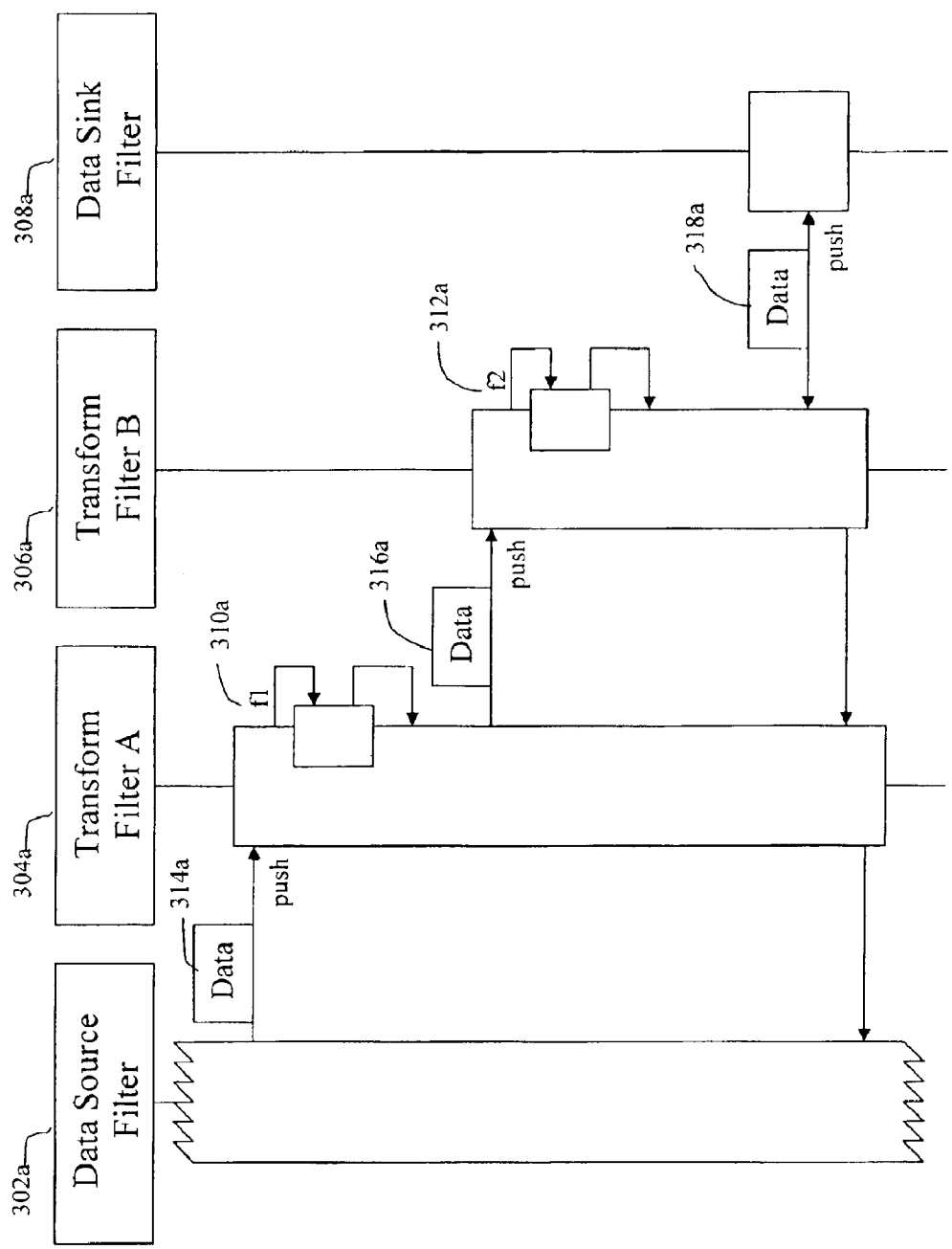
Fig. 7-A

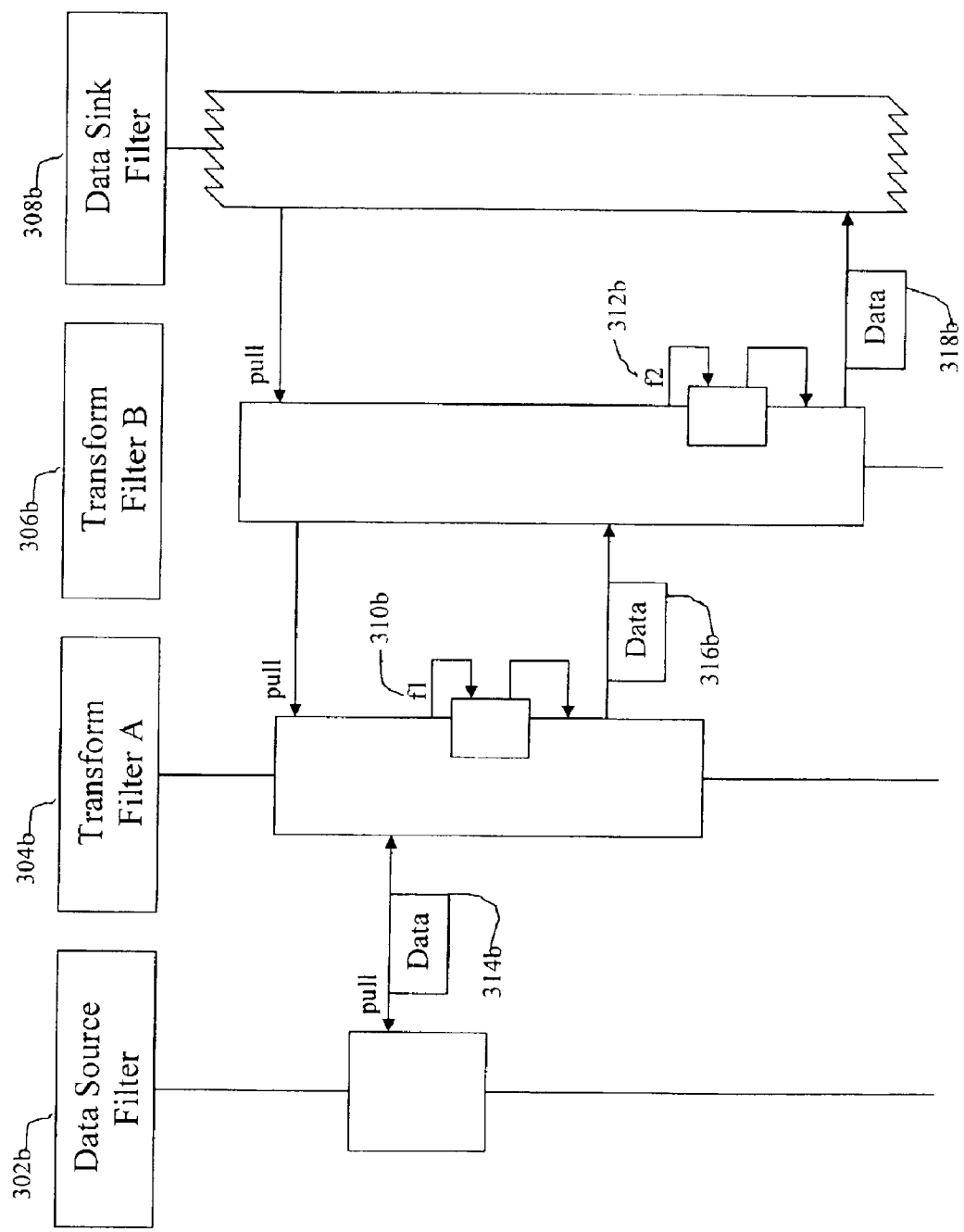
Fig. 7-B

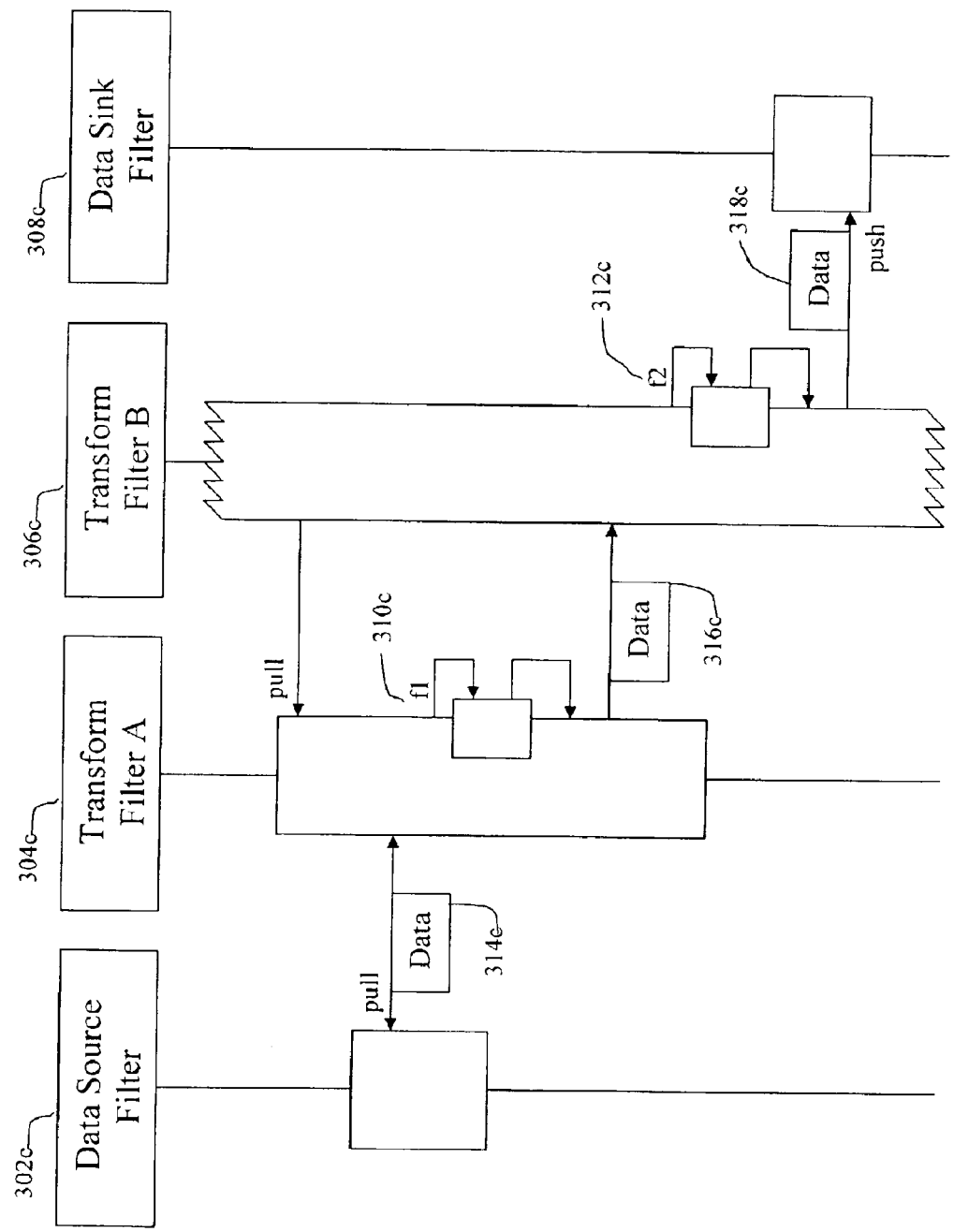
Fig. 7-C

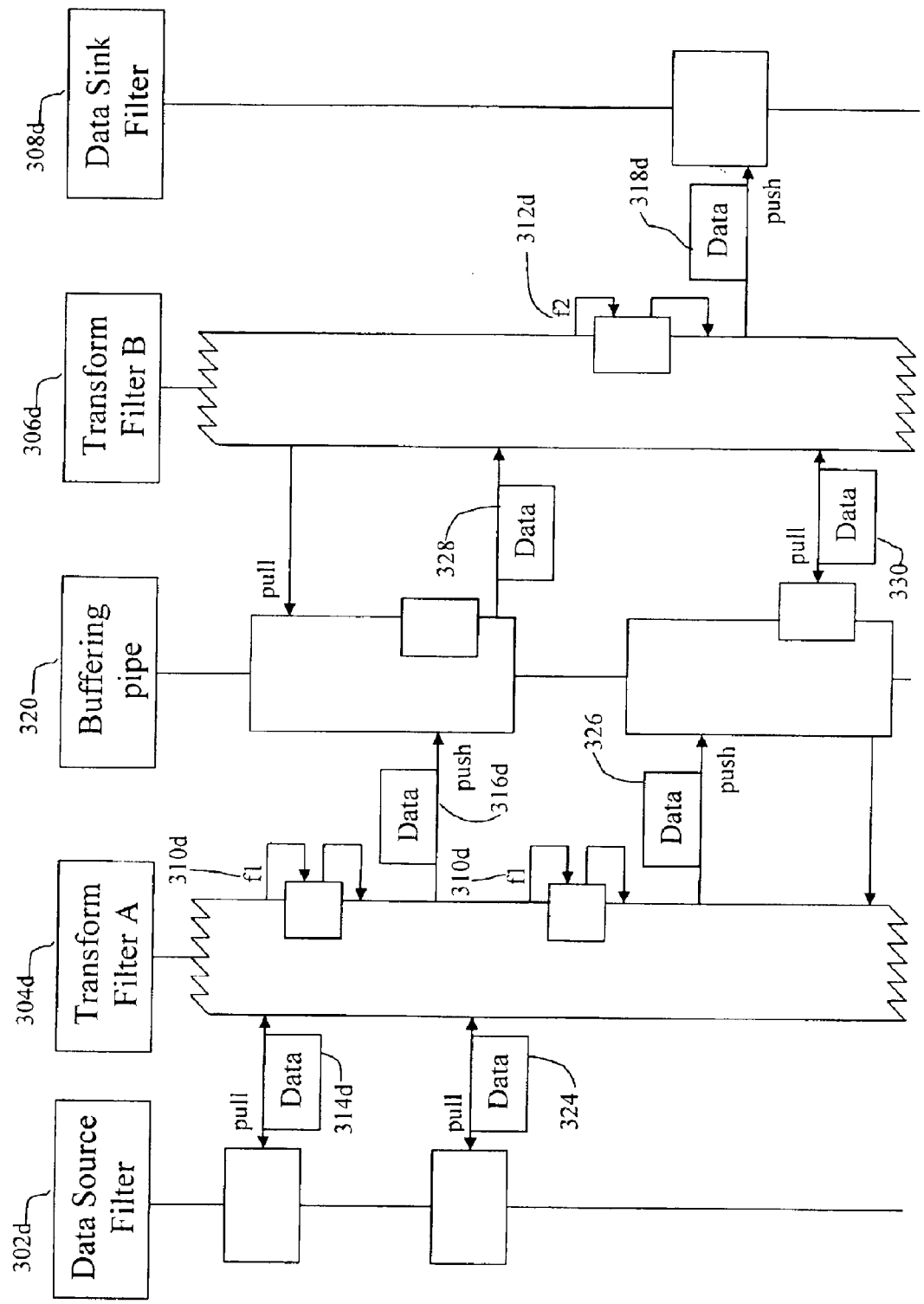
Fig. 7-D

DIAGNOSTIC MEDICAL ULTRASOUND SYSTEM HAVING A PIPES AND FILTERS ARCHITECTURE

REFERENCE TO RELATED APPLICATIONS

The following and commonly assigned U.S. Patent Application has been filed on the same date as the present application. This application relates to and further describes other aspects of the embodiments disclosed in the present application and is herein incorporated by reference.

U.S. patent application Ser. No. 10/393,091, now U.S. Pat. No. 6,733,449 "SYSTEM AND METHOD FOR REAL-TIME STREAMING OF ULTRASOUND DATA TO A DIAGNOSTIC MEDICAL ULTRASOUND STREAMING APPLICATION", filed herewith.

BACKGROUND

Diagnostic medical ultrasound systems are routinely used in medical applications for the purpose of imaging various body tissues and organs and for other diagnostic and therapeutic purposes. These systems allow medical professionals to view the internal conditions of a patient thereby enabling them to render a better diagnosis. In one example of a diagnostic medical ultrasound system, a piezoelectric transducer acquires image data by transmitting a series of ultrasonic pulses into a patient and receiving the echoes therefrom. These echoes are converted/manipulated into an image and displayed on a monitor or stored for later use. This process can be further characterized as a continuous or streamed process. As the echoes are received by the transducer, they are converted and displayed in a continuous fashion, i.e., streamed from the transducer to the display.

The ultrasound system is primarily designed to process the received echoes in this streaming fashion. To improve the functionality of the ultrasound system, applications may be provided which post-process the received echoes to enhance the usability of the data. For example, color coding may be added to further enhance the visibility of Doppler shifts in the echoes. Any post processing of the received echo information must either operate in a streamed fashion, i.e. operate on the received echo data as it is received in real time, or buffer/store a portion of the received echo data and operate on that buffered/stored portion.

Development of applications which can operate in real time on the received echo information is complex and resource intensive, such that the number of such streaming applications offered on a given ultrasound system is often limited. Furthermore, many of today's applications rely heavily on expensive custom hardware components specifically designed to perform data processing, such as a 3D imaging calculator. Use of these hardware components limits the reusability and flexibility of the application and the ultrasound system. The hardware components also typically tie up any ultrasound data being processed until a final result is produced, thereby preventing multiple applications from operating in parallel. Further, these applications are typically structured based on the nature of ultrasound system itself, i.e. the application's functionality is divided among three functions: acquisition of data, manipulation of data and storage or display of the manipulated data. Typically, the application developer, in designing the software architecture of the application, makes initial assumptions about each function's role in the application. For example, the data acquisition function might assume that a certain piece of hardware in the ultrasound system was always going to be used. It may then use global data structures that are very specific to this piece of hardware. The acquisition function would then acquire data, place it into and control it with one of these global data structures. The data manipulation and storage functions would then need to access these global data structures in order to retrieve both control and ultrasound imaging data to perform their tasks. In this way, all three functions have become dependent on a specific piece of hardware. Should that hardware change, or any control information in the highly coupled data structure change, all three functions would need to be modified. Another example of functional co-dependency is a simple in-process frame grabbing application. A data source acquisition function might always assume it will acquire the same kind of data and that this data will always be compressed and stored in the same particular way. As a result, the acquisition function would be coded in a way to take advantage of these assumptions, typically for performance reasons. If either the data manipulation or data storage function changed, it would likely break the acquisition function. If a need arises to make data storage out-of process, it is likely to have significant impact on both data acquisition and manipulation because both assumed that the whole application would be handled in-process. In sum, the more assumptions made, the more dependent each function becomes on the other two and the more difficult application development and maintenance becomes.

FIG. 1A shows one example of a monolithic ultrasound streaming application. As known in the art, a monolithic program is a program with very few classes or structures. These classes or functions exhibit a high degree of physical and data coupling between one another. In such an application, each of the three functions, i.e. acquisition $2a$, manipulation $4a$ and storage $6a$, is coupled to each of the other two because many initial assumptions are made. For example, data acquisition $2a$ is dependent on both data manipulation $4a$ and data storage $6a$. When a change is made to any of the functions, each of the other two functions must be corrected accordingly. Thus, all of the functions must be recompiled and tested when a change is made to any function. Furthermore, each function does not have clear responsibilities. Each function may be responsible for more or less than its name implies. It is typically more cost-effective to write an entirely new application instead of fixing problems with a monolithic ultrasound streaming application because of the problems associated with coupling and the lack of clear responsibilities. Finally, the functions of a monolithic ultrasound streaming application are not reusable because so many assumptions are made and the individual processing steps are buried in the bulky mass of programming code.

FIG. 1B shows an example of a modular ultrasound streaming application. In a modular ultrasound streaming application, modules have been created that clearly define the responsibilities of each function. Each function also has a well defined Application Programming Interface, or API. Here, the dependencies of each function have been reduced. However, acquisition $2b$ is still dependent on manipulation $4b$, which is still dependant on storage $6b$. In this scenario, an alteration in the data storage $6b$ function will still require the manipulation $4b$ and acquisition $2b$ functions to be recompiled, re-linked and retested. Although alterations to a modular ultrasound streaming application are less expensive than in monolithic ultrasound streaming applications, alterations can still be costly. Furthermore, modular applications are not easily reusable as the various functions are still buried in large amount of programming code.

While such applications provide a valuable diagnostic tool to physicians, they also suffer from inherent limitations and may make real-time data processing at minimum difficult, if not impossible, to complete without extensive testing and cost. Furthermore, these applications are not designed to be reusable and do not allow access to intermediate data.

Accordingly, there is a need for a flexible, reusable, low cost ultrasound streaming application architecture that reduces dependency on custom hardware components and legacy programs while making ultrasound data readily available at any point throughout the course of processing. Further, there is a need for an ultrasound streaming application architecture that further reduces the number of initial programming assumptions made in development, thereby reducing dependencies between the underlying functions of the application.

SUMMARY

The present invention is defined by the following claims, and nothing in this section should be taken as a limitation on those claims. By way of introduction, the preferred embodiments described below relate to a component for use with a diagnostic medical ultrasound system comprising an input source operative to provide a sequence of digital signals, each of the sequence of digital signals having been derived from at least one ultrasonic echo received by an ultrasound transducer from a subject in response to transmission of acoustic energy into said subject by said transducer, at least one processor coupled with the input source and comprising an incremental data processing architecture for executing a first application program, the first application program operative to incrementally receive and process each of at least a subset of the sequence of digital signals in succession and an output sink coupled with the at least one processor and operative to receive the processed digital signals from the first application program.

In another aspect, the present invention relates to a method of operating a diagnostic medical ultrasound system. The method comprises receiving a sequence of digital signals, each of the sequence of digital signals having been derived from an ultrasonic echo received by an ultrasound transducer from a subject in response to transmission of acoustic energy into said subject by the transducer, executing a first application program on at least one processor coupled with the input source, the at least one processor comprising an incremental data processing architecture, receiving and processing incrementally, by the first application program, each of at least a subset of the sequence of digital signals in succession and transmitting the processed digital signals from the first application to an output sink coupled with the at least one processor.

Further aspects and advantages of the invention are discussed below in conjunction with the preferred embodiments.

BRIEF DESCRIPTION OF THE DRAWINGS

FIG. 1A depicts a representation of a monolithic ultrasound streaming application as is known in the art.

FIG. 1B depicts a representation of a modular ultrasound streaming application as is known in the art.

FIG. 7A depicts a representation of an exemplary data flow of a push pipeline of a pipes and filters architecture according to one embodiment.

FIG. 7B depicts a representation of an exemplary data flow of a pull pipeline of a pipes and filters architecture according to one embodiment.

FIG. 7C depicts a representation of an exemplary data flow of a mixed push-pull pipeline of a pipes and filters architecture according to one embodiment.

FIG. 7D depicts a representation of an exemplary data flow of a mixed push-pull pipeline of one embodiment of a pipes and filters architecture incorporating a buffering pipe.

DETAILED DESCRIPTION OF THE PRESENTLY PREFERRED EMBODIMENTS

Figure 2:
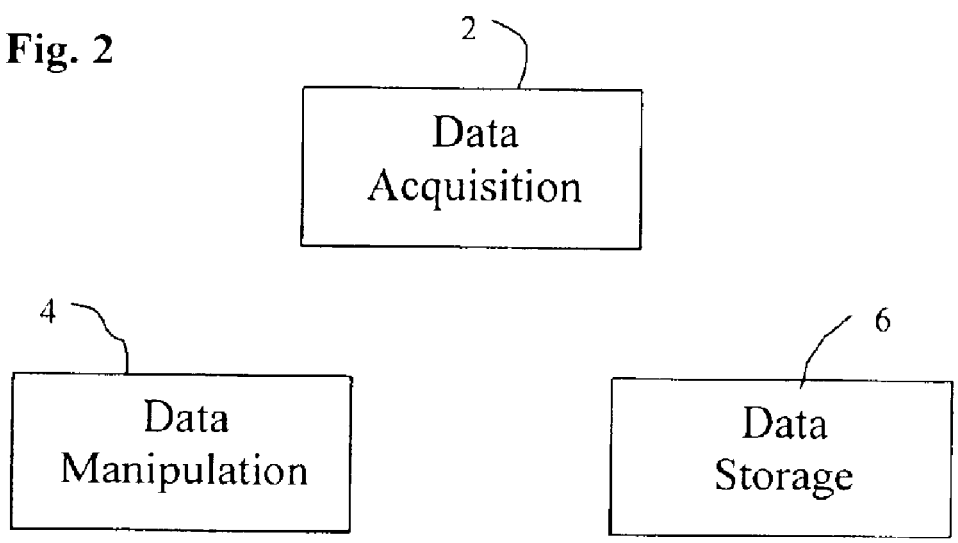
FIG. 2 depicts a representation of one embodiment of an ultrasound streaming application based on the pipes and filters framework.

As shown in FIG. 2, the disclosed embodiments relate to a an ultrasound application in which each of the three underlying functions of acquisition, manipulation and storage are decoupled from each other. FIG. 2 represents the data dependencies of an ultrasound streaming application using the pipes and filters framework disclosed herein. As can be seen, data acquisition 2, data manipulation 4 and data storage 6 operate with virtually no coupling. Furthermore, the disclosed embodiments eliminate the dependencies of these functions by taking advantage of the object oriented programming principles of encapsulation, inheritance and polymorphism. Encapsulation allows the internal implementation of the object to be modified without requiring any change to the application that uses it. In the disclosed embodiments, the responsibilities of the underlying functions of the framework are clearly defined and encapsulated in classes. Inheritance enables an application developer to develop abstract objects to establish the roles of each underlying function, and then develop subclasses based on those abstract objects for specific embodiments of the present invention. Finally, polymorphism allows the disclosed embodiments to produce different results based on the specific objects that are provided, creating greater flexibility. Thus, encapsulation, inheritance and polymorphism allow the functions of an ultrasound streaming application to be compiled and tested in isolation before being integrated into the overall system. Furthermore, new modules designed to enhance or extend the behavior of the application can be integrated easily into an existing application. Finally, new applications can be developed quickly as modules that fit into a generic framework can be reused and incorporated into a new application.

Figure 3:
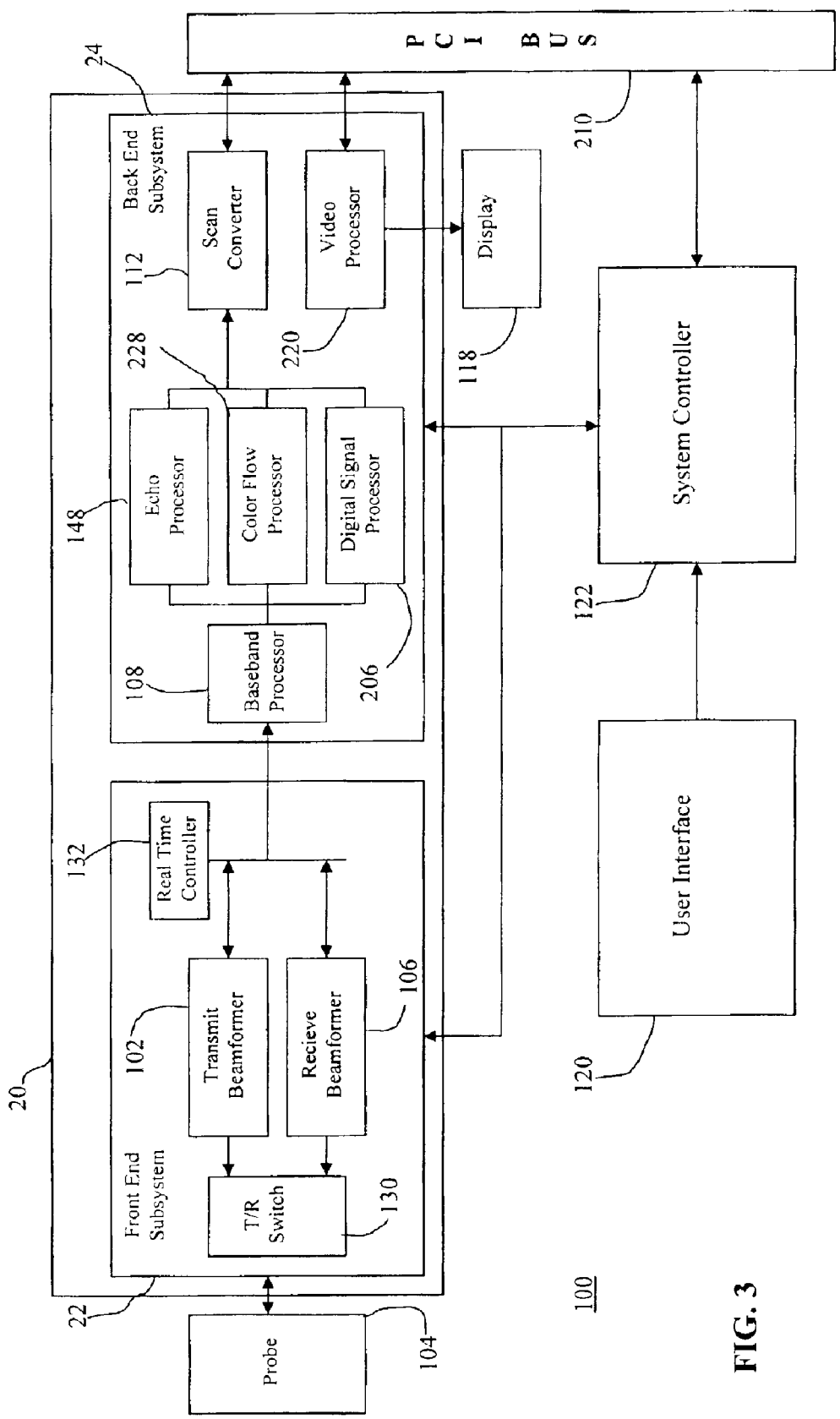
FIG. 3 depicts a block diagram of a diagnostic medical ultrasound system according to the one embodiment.

FIG. 3 shows one embodiment of a diagnostic medical ultrasound system 100. The depicted architecture corresponds to the architecture of the Sonoline Antares™ Ultrasound Platform manufactured by Siemens Medical Solutions USA, Inc., located in Iselin, N.J. It will be appreciated that one or more of the described components may be implemented in hardware, software or a combination thereof. The ultrasound system 100 includes an ultrasonic imaging probe or transducer 104, acquisition hardware 20, a front end acquisition hardware subsystem 22, a back end acquisition hardware subsystem 24, a user interface 120, a system controller 122 and a display 118. In one embodiment, the back end subsystem 24 comprises a baseband processor 108, an echo processor 148, a color flow processor 228, a digital signal processor 206, a scan converter 112 and a video processor 220. In one embodiment, the exemplary front end acquisition hardware 22 includes a transmit beamformer 102, a receive beamformer 106, a transmit/receive switch 130, and a real time controller 132. As will be discussed below, the front end acquisition hardware 22 may alternatively include local or remote optical or magnetic data storage devices such as a computer memory, hard disk, CD, DVD or video tape recorder coupled with the ultrasound system 100 via a wired or wireless device or network interface. Herein, the phrase "coupled with" is defined to mean directly connected to or indirectly connected through one or more intermediate components. Such intermediate components may include both hardware and software based components.

The front end acquisition hardware 22 is coupled with the transducer 104. The front-end acquisition hardware 22 causes the transducer 104 to generate acoustic energy into a subject and receives the electrical signals generated by the transducer 104 in response to the received echoes representing a two dimensional representation of the subject. In one embodiment, the front end acquisition hardware 22 is configurable to acquire information corresponding to a plurality of two-dimensional representations or image planes of a subject for three-dimensional reconstruction. Other configurations, such as those for acquiring data with a two dimensional, 1.5 dimensional or single element transducer array, may be used. To generate each of the plurality of two-dimensional representations of the subject during an imaging session, the acquisition hardware 20 is configured to transmit, receive and process during a plurality of transmit events. Each transmit event corresponds to firing acoustic energy along one or more ultrasound scan lines in the subject. As a result of the succession of transmit events occurring during use of the system 100, information is received continuously throughout this process. The constant flow of data generated by the acquisition hardware 20 can be characterized as a stream of data.

Data streams, such as those generated by the acquisition hardware 20 described above, are characterized by properties, such as the data format, the transmission or acquisition rate, the number of image bytes per sample, etc. Depending on the type of data being represented the data format may be different. Different streams may also be transmitted at different rates. The number of image bytes per sample may also be different depending on the type of data represented. For example, physiological and Doppler derived waveforms may have a constant number of image bytes per sample while the number of image bytes per sample may be programmable for 2D streams. Additional properties of streams may include a source property and a sink property. Each stream must have a source and a sink, the source being the location from which the stream originates and the sink being the location where the stream terminates. Sources may be further characterized as being "live" or "stored". A live source is a source which is actually generating the stream, typically in real time, while a stored source is a source which stores a representation of a stream created at an earlier time. The stream sink may be the display, CPU memory or other storage or processing device. A stream may also be classified as a "clone" of another stream. Cloned streams are copies of streams used to provide multiple applications 40 with access to a particular stream's data. The original stream will be "owned" by the first application who gains access to it, meaning that application will be able to alter various stream properties, such as acquisition rate. An application can alter these properties by communicating with the actual data source acquiring the information, either directly or through an ultrasound stream manager as described below. If another application 40 desires the data contained in the same stream, a clone will be made. In one embodiment, a cloned stream differs from a copy of a stream in that the cloned stream's properties depend on the properties of the original stream. The second application 40 receiving the cloned stream is not permitted to communicate directly with the acquisition hardware as it does not own the stream. In other words, the application 40 processing the cloned stream is only permitted to alter the cloned streams properties within the boundaries of the properties of the original stream. In contrast, some or all of the properties of a copy of a stream may be altered independently of the original stream. For example, if the application 40 controlling a live stream configures the acquisition hardware 20 to acquire data at 8 bits per second, the cloned stream will also be provided with data at 8 bits per second. It should be noted, however, that a cloned stream can be manipulated to represent data samples at various rates other than that of the live stream. For example, a cloned stream can be "sped up" or "slowed down" through interpolation or frame dropping, as know in the art. Depending on the desired stream contents, a stream's type may be set as a pixel, waveform, or audio and video sample. It will be appreciated that other stream types may be used depending on the implementation.

In one embodiment, nine different types of streams are capable of interacting within the disclosed pipes and filters framework, as will be discussed below. The individual properties of a stream correspond to that stream's number. Streams can be either 2d streams, trace streams, video streams or waveform streams. 2D streams are used for two dimensional image data generated by the transducer. 2D streams are also used to display B-mode images and can be utilized by panoramic imaging, 3D imaging and equalization applications. Trace streams are used for displaying Doppler and M-Mode data. Video streams are used to display digital imaging and communications in medicine, or DICOM, clips. Waveform streams are used for Physiological Waveforms and Doppler derived waveforms as well as displaying ECG/EKG signals. Additionally, each waveform stream is capable of acquiring and displaying, i.e. contains sufficient bandwidth for two waveforms. For example, in one embodiment streams 0, 1 and 2 are used to denote 2D streams of ultrasound data. Stream 3 can be used to display either another 2D stream or a Trace display. Stream 4 is used for a Trace stream. Streams 5, 6 and 7 are used for physiological streams. Thus, six A & B physiological waveforms are capable of being displayed. Finally, stream 8 represents a waveform stream reserved for Doppler imaging.

The transmit beamformer 102 is coupled with the transducer 104 and is of a construction known in the art, such as a digital or analog based beamformer capable of generating signals at different frequencies. The transmit beamformer 102 generates one or more excitation signals which causes the transducer 104 to emit one or more ultrasonic pulses. Each excitation signal has an associated center frequency. As used herein, the center frequency represents the frequency in a band of frequencies approximately corresponding to the center of the amplitude distribution. Preferably, the center frequency of the excitation signals is within the 1 to 15 MHz range and accounts for the frequency response of the transducer 104. The excitation signals have non-zero bandwidth.

It will be appreciated that alternative methods of generating and controlling ultrasonic energy as well as receiving and interpreting echoes received therefrom for the purpose of diagnostic imaging, now or later developed, may also be used with the disclosed embodiments in addition to or in substitution of current beamforming technologies. Such technologies include technologies which use transmitters and/or receivers which eliminate the need to transmit ultrasonic energy into the subject along focused beam lines, thereby eliminating the need for a transmit beamformer, and may permit beam forming to be performed by post processing the received echoes. Such post-processing may be performed by a receive beamformer or by digital or analog signal processing techniques performed on the received echo data. For example, please refer to U.S. patent application Ser. No. 09/518,972, entitled "METHOD AND APPARATUS FOR FORMING MEDICAL ULTRASOUND IMAGES", now U.S. Pat. No. 6,309,356 and U.S. patent application Ser. No. 09/839,890, entitled "METHOD AND APPARATUS FOR FORMING MEDICAL ULTRASOUND IMAGES". now U.S. Pat. No. 6,551,246, the disclosures of which are herein incorporated by reference.

Control signals are provided to the transmit beamformer 102 and the receive beamformer 106 by the real time controller 132. The transducer 104, as controlled by the transmit beamformer 102, is caused to fire one or more acoustic lines in each transmit event, and the receive beamformer 106 is caused to generate in-phase and quadrature (I and Q) information along one or more scan lines. Alternatively, real value signals may be generated. A complete frame of information corresponding to a two-dimensional representation (a plurality of scan lines) is preferably acquired before information for the next frame is acquired. The real time controller 132 is also used to manage the data flow created by the receive beamformer as it collects image information, making the stream of data available to the back end subsystem 22.

Upon the firing of one or more ultrasound scan lines into the subject, some of the acoustical energy is reflected back to the transducer 104. This reflected acoustical energy is detected by the transducer 104 and converted into electrical signals which are passed to the receive beamformer 106. In addition to receiving signals at the fundamental frequency (i.e., the same frequency as that transmitted), the non-linear characteristics of tissue or optional contrast agents also produce responses at harmonic frequencies. Harmonic frequencies are frequencies associated with non-linear propagation or scattering of transmit signals. As used herein, harmonic includes subharmonics and fractional harmonics as well as second, third, fourth, and other higher harmonics. Fundamental frequencies are frequencies corresponding to linear propagation and scattering of the transmit signals of the first harmonic. Non-linear propagation or scattering corresponds to shifting energy associated with a frequency or frequencies to another frequency or frequencies. The harmonic frequency band may overlap the fundamental frequency band.

The baseband processor 108 is coupled with the receive beamformer 106 and receives the converted electrical signals representative of the reflected acoustical energy. The baseband processor 108 passes information associated with a desired frequency band, such as the fundamental band or a harmonic frequency band. In one embodiment, the baseband processor 108 may be included as part of the receive beamformer 106. Furthermore, the baseband processor 108 demodulates the summed signals to baseband. The demodulation frequency is selected in response to the fundamental center frequency or another frequency, such as a second harmonic center frequency. For example, the transmitted ultrasonic waveforms are transmitted at a 2 MHz center frequency. The summed signals are then demodulated by shifting by either the fundamental 2 MHz or the second harmonic 4 MHz center frequencies to baseband (the demodulation frequency). Other center frequencies may be used. Signals associated with frequencies other than near baseband are removed by low pass filtering. As an alternative or in addition to demodulation, the baseband processor 108 provides band pass filtering. The signals are demodulated to an intermediate frequency (IF) (e.g. 2 MHz) or not demodulated and a band pass filter is used. Thus, signals associated with frequencies other than a range of frequencies centered around the desired frequency or an intermediate frequency (IF) are filtered from the summed signals. The demodulated or filtered signal is passed to the additional processors 148, 228 and 206 as either the complex I and Q signal or other types of signals, such as real value signals. It should be noted that band pass "filtering", as well as other types of data filtering known in the art, should not be confused with the filter elements of the pipes and filters framework disclosed herein. As known in the art, "filtering" data involves allowing data with certain characteristics to pass while blocking data without those characteristics. On the other hand, while the filter elements discussed below may perform functions similar to those provided by the band pass processor 108, the filter elements, as used by the architecture described herein, are more general processing stages that manipulate, transform or enrich streaming data.

By selectively filtering which frequencies are received and processed, the backend subsystem 22 produces images with varying characteristics. In tissue harmonic imaging, no additional contrast agent is added to the target, and only the nonlinear characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible.

Tissue harmonic images provide a particularly high spatial resolution and often possess improved contrast resolution characteristics. In particular, there is often less clutter in the near field. Additionally, because the transmit beam is generated using the fundamental frequency, the transmit beam profile is less distorted by a specific level of tissue-related phase aberration than a profile of a transmit beam formed using signals transmitted directly at the second harmonic.

The harmonic imaging technique described above can be used for both tissue and contrast agent harmonic imaging. In contrast agent harmonic imaging, any one of a number of well known nonlinear ultrasound contrast agents, such as micro-spheres or the Optison™ agent by Nycomed-Amersham of Norway, are added to the target or subject in order to enhance the non-linear response of the tissue or fluid. The contrast agents radiate ultrasonic energy at harmonics of an insonifying energy at fundamental frequencies.

The echo 148, color flow 228 and digital signal 206 processors are coupled with the baseband processor 108 and receive the filtered signals from the transducer 104/receive beamformer 106. The digital signal processor 206 comprises one or more processors for generating two-dimensional Doppler or B-mode information. For example, a B-mode image, a color Doppler velocity image (CDV), a color Doppler energy image (CDE), a Doppler Tissue image (DTI), a Color Doppler Variance image, or combinations thereof may be selected by a user. The digital signal processor 206 detects the appropriate information for the selected image. In one embodiment, the digital signal processor 206 is adapted for Doppler processing and a B-mode processing. As known in the art, the Doppler processing estimates velocity, variance of velocity and energy from the I and Q signals. As known in the art, the B-mode processing generates information representing the intensity of the echo signal associated with the I and Q signals. The echo processor 148 performs baseband and amplitude mode signal processing of RF and IQ data in a known manner. The color flow processor 228 adds color to the acquired information, as known in the art.

The information generated by the echo 148, color flow 228 and digital signal 206 processors is provided to the scan converter 112. Alternatively, the scan converter 112 includes detection processes as known in the art and described in U.S. Pat. No. 5,793,701 entitled "METHOD AND APPARATUS FOR COHERENT IMAGE FORMATION", assigned to the assignee of the present invention, the disclosure of which is herein incorporated by reference. The scan converter 112 is of a construction known in the art for arranging the output of the signal processors 148, 228 and 206 into two-dimensional representations or frames of image data. The scan converter 112 converts acoustic ultrasound line data, typically in a polar coordinate system, into data which may be plotted on a Cartesian grid. Using volume averaging or other similar algorithms on the returned echo data, the slice information is merged into a single 2D plane. This permits display of the ultrasound image on a two-dimensional output device such as a display monitor 118. Preferably, the scan converter 112 outputs formatted video image data frames, using a format such as the DICOM Medical industry image standard format or a TIFF format. Thus, the plurality of two-dimensional representations is generated. Each of the representations corresponds to a receive center frequency, such as a second harmonic center frequency, a type of imaging, such as B-mode, and positional information. The harmonic based representations may have better resolution and less clutter than fundamental images. By suppressing the harmonic content of the excitation signal, the benefits of harmonic imaging of tissue may be increased. In any event, the scan converter 112 provides its output to the PCI bus 210. In one embodiment, the PCI bus 210 is a standard peripheral component interconnect board, as known.

The user interface 120 is coupled with the system controller 122 and includes one or more input devices which the clinician/sonographer/physician uses to interface with the ultrasound system 100. The user interface 120 includes input devices such as a keyboard, mouse, trackball, touch screen or other input devices or combinations thereof as are known in the art. Further the user interface 120 may also include graphic user interface ("GUI") elements coupled with the input devices and with the display 118 for both input and output functions. In addition to controlling the ultrasound functions of the ultrasound system 100, the user interface 120 may afford the user the opportunity to modify graphical representations, imaging planes and displays produced by the ultrasound system 100. Finally, the user interface 120 allows the user to coordinate multiple ultrasound probes 104.

The system controller 122 is coupled with the front end subsystem 22, the backend subsystem 22, the PCI bus 210 and the user interface 120 and controls and coordinates the functions of the ultrasound subsystems. The term "system controller" broadly refers to the appropriate hardware and/or software components of the ultrasound system 100 that can be used to implement the preferred embodiments described herein. It should be understood that any appropriate hardware (analog or digital) or software can be used and that the embodiments described herein can be implemented exclusively with hardware. Further, the system controller 122 can be separate from or combined with (in whole or in part) other processors of the ultrasound system 100 (including attendant processors), which are not shown in FIG. 3 for simplicity.

The various elements of the ultrasound system including the front end subsystem 22, backend subsystem 24 and user interface 120 are controlled in real time by the system controller 122. The system controller 122 controls the operation of the components of the system 100. A user, via the user interface 120, can adjust imaging parameters such as, but not limited to, image depth, image width, and frame rate. The controller 122 interprets the set-up information entered by the user and configures the components of the system 100 accordingly.

The video processor 220 acts as an interface between the system controller 122 and the display 118. In various embodiments, the video processor 220 can be configured to work with a variety of display types, such as cathode ray tubes or liquid crystal displays. The video processor 220 can also be configured to output information to a printer, memory, storage device, such as a computer storage device or a video recorder, computer network or other means for communicating data representative of an ultrasonic echo known in the art. The display monitor 118 is connected to the display controller 116 and is a standard display monitor as known in the art. In alternate embodiments, the display 118 can be replaced with a printer, memory, storage device, or any other output device known in the art.

Figure 4:
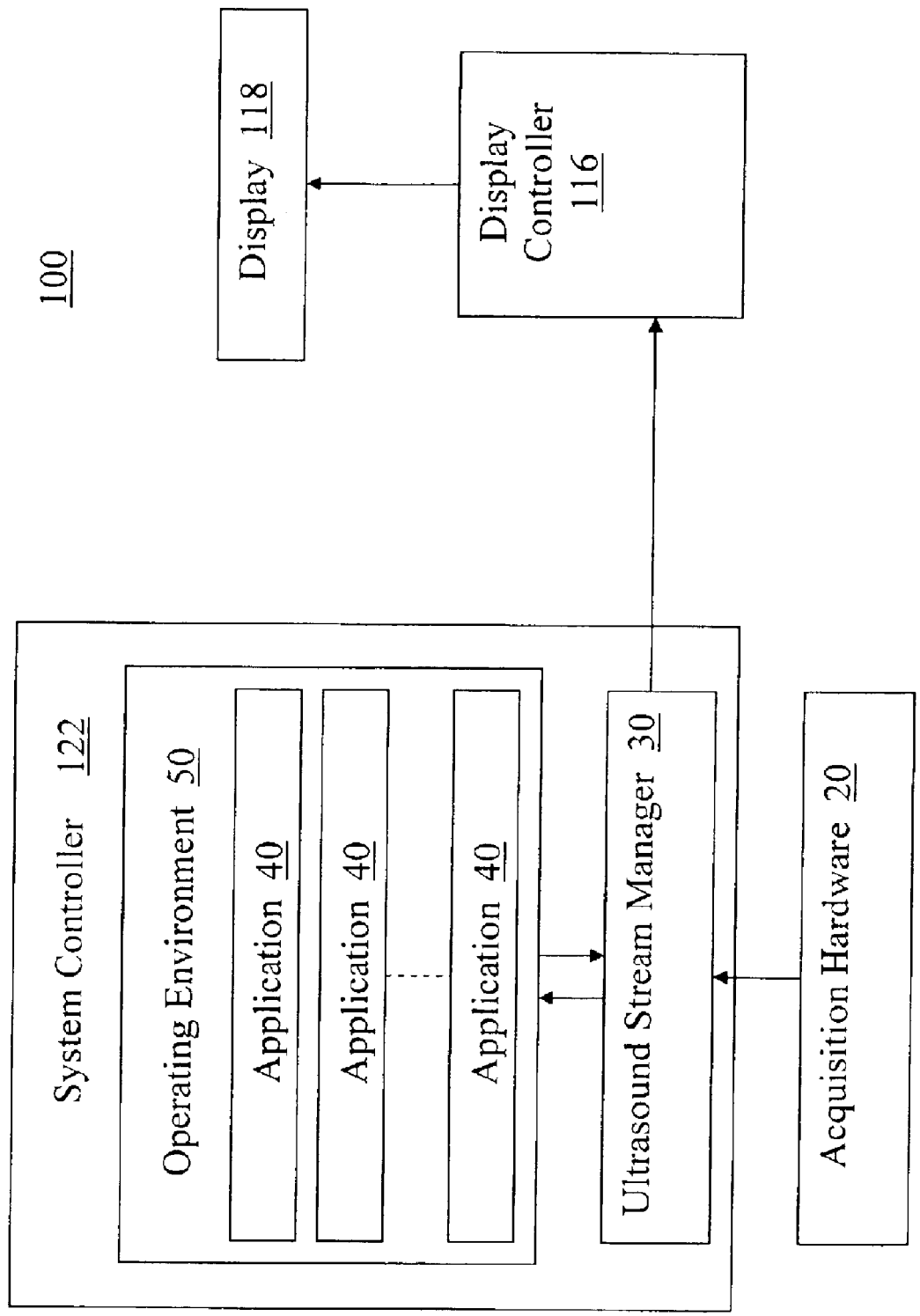
FIG. 4 depicts a logical block diagram of the diagnostic medical ultrasound system of FIG. 3.

FIG. 4 shows one embodiment of the logical structure of the system controller 122 and the data flow of one embodiment of the diagnostic medical ultrasound system 100. As discussed above, the system 100 includes the acquisition hardware 20, the system controller 122, the display controller 116 and the display 118. In one embodiment, the system controller 122 logically includes an ultrasound stream manager 30, and an operating environment 50. The acquisition hardware 20 is coupled with the ultrasound stream manager 30 and acquires ultrasound data and provides the data in the streaming fashion discussed above to the ultrasound stream manager 30. In an alternate embodiment, the acquisition hardware 20 may include a storage device, such as a computer disk drive or video recorder, which stores previously acquired ultrasound data.

The ultrasound stream manager 30 is further coupled with the display controller 116 and the operating environment 50 and acts as the interface between the acquisition hardware 20, the operating environment 50 and the display controller 116. Effectively, the ultrasound stream manager 30 is an Application Programming Interface ("API") to the ultrasound system 100 and manages the inputs and outputs of the operating environment 50, providing data inputs from the acquisition hardware 20, and facilitating data output to the display controller 116, or other output or storage device coupled with the system locally or via a network. It should be noted that while the embodiments described herein comprise an ultrasound stream manager 30 working with an ultrasound streaming application utilizing a pipes and filters framework, the disclosed ultrasound stream manager 30 may also be used with non-pipes and filters based applications and frameworks and is capable of interacting with multiple applications of various types. Furthermore, the pipes and filters applications and framework disclosed herein may be implemented so as access system resources without using the ultrasound stream manager 30. In one embodiment, outputs from the operating environment 50 may be provided, via the ultrasound stream manager 30, to the acquisition hardware 20, such as for use in control feedback applications. The ultrasound stream manager 30 provides an abstracted interface between the operating environment 50 and various sources of data within the ultrasound system 100. In one embodiment, these sources of data include the user interface 120, imaging probe 104 output, receive beamformer 106 output, baseband processor 108 output, echo processor 148 output, color flow processor 228 output, digital signal processor 206 output, pre-scan converter 112, post scan converted 112, or audio and video streams from the video processor 202 output. Additional hardware may be provided for acquiring waveform streams such as ECG/EKG streams. It will be appreciated that the ultrasound stream manager 30 may provide abstracted interfaces, as described herein, to any point within the ultrasound system 30. For example, an interface may be provided to the raw data stream prior to processing by the receive beamformer 106, prior to processing by the filter block 108, prior to Doppler 146 or B-Mode 148 processing and/or prior to scan conversion.

In one embodiment, the ultrasound stream manager 30 forwards the live display stream provided by acquisition hardware 20, to the display controller 116 for substantially immediate display. Substantially simultaneously, the data from the acquisition hardware 20 is made available to the operating environment 50 of the system processor 122 for further processing, as will be described below. In an alternate embodiment, the user may select whether to view the live display stream or to view the live display stream in combination with or in place of the processed display stream (described below). In yet another embodiment, the user may also select whether to display multiple processed streams, the disclosed embodiments being capable of displaying such streams synchronously. In one embodiment, the ultrasound stream manager 30 is implemented as combination of software and hardware. It will be appreciated, however, that the ultrasound stream manager 30 may be implemented entirely in software or entirely in hardware.

The operating environment 50 is a logical environment in which ultrasound applications operate, receiving and/or processing ultrasound data and optionally generating one or more data outputs. The operating environment 50 is an architecture which defines operating rules and provides programmatic constructs, e.g. the ultrasound stream manager 30, for interfacing with the ultrasound system 100. Effectively, the operating environment 50 is similar to the operating system of a conventional personal computer. The operating environment 50 generally comprises one or more applications 40 that process the ultrasound data streams optionally provided by the ultrasound stream manager 30 or provided directly from the acquisition or storage hardware. The processed ultrasound data streams from the applications 40 are then directly forwarded to the display controller 116 or other outputs (not shown) or optionally provided back to the ultrasound stream manager 30 in order to be forwarded to the display controller 116 or other outputs (not shown). Utilizing the data flow of this embodiment, the display 118 is able to display both the raw image produced by acquisition hardware 20 as well as the information processed by the system controller 122, i.e. the one or more applications 40, in real-time. In alternate embodiments, other output devices may be provided in addition to or in place of the display 118, such as alternative output devices such as printer or projector, storage devices such as a CD, DVD or video recorder, computer storage device, a remote network device, a CPU buffer of an ultrasound system, a memory, or software components such as another application 40.

Figure 5:
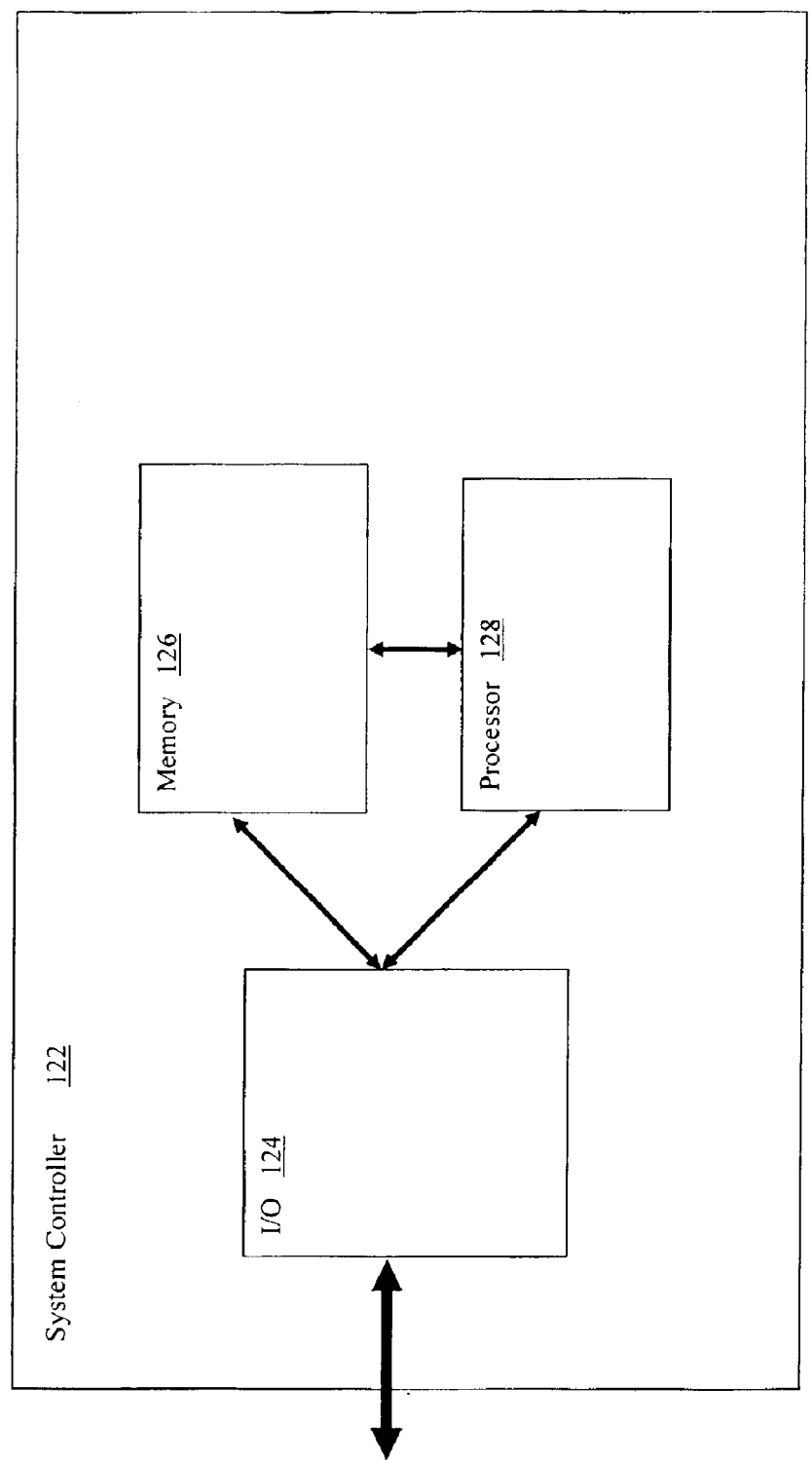
FIG. 5 depicts a block diagram of one embodiment of a system controller component for use with the diagnostic medical ultrasound system of FIG. 3.

FIG. 5 shows one embodiment of the physical structure of the system controller 122. The system controller 122 comprises an input/output controller 124, a memory 126 and a processor 128. In one embodiment, the system controller 122 is that used by the Antares model 5936518 ultrasound system, manufactured by Siemens Medical Solutions, USA, located in Iselin, N.J., described above. The Antares system includes a general purpose processing unit configurable by known methods to incorporate the functionality disclosed herein.

Figure 6:
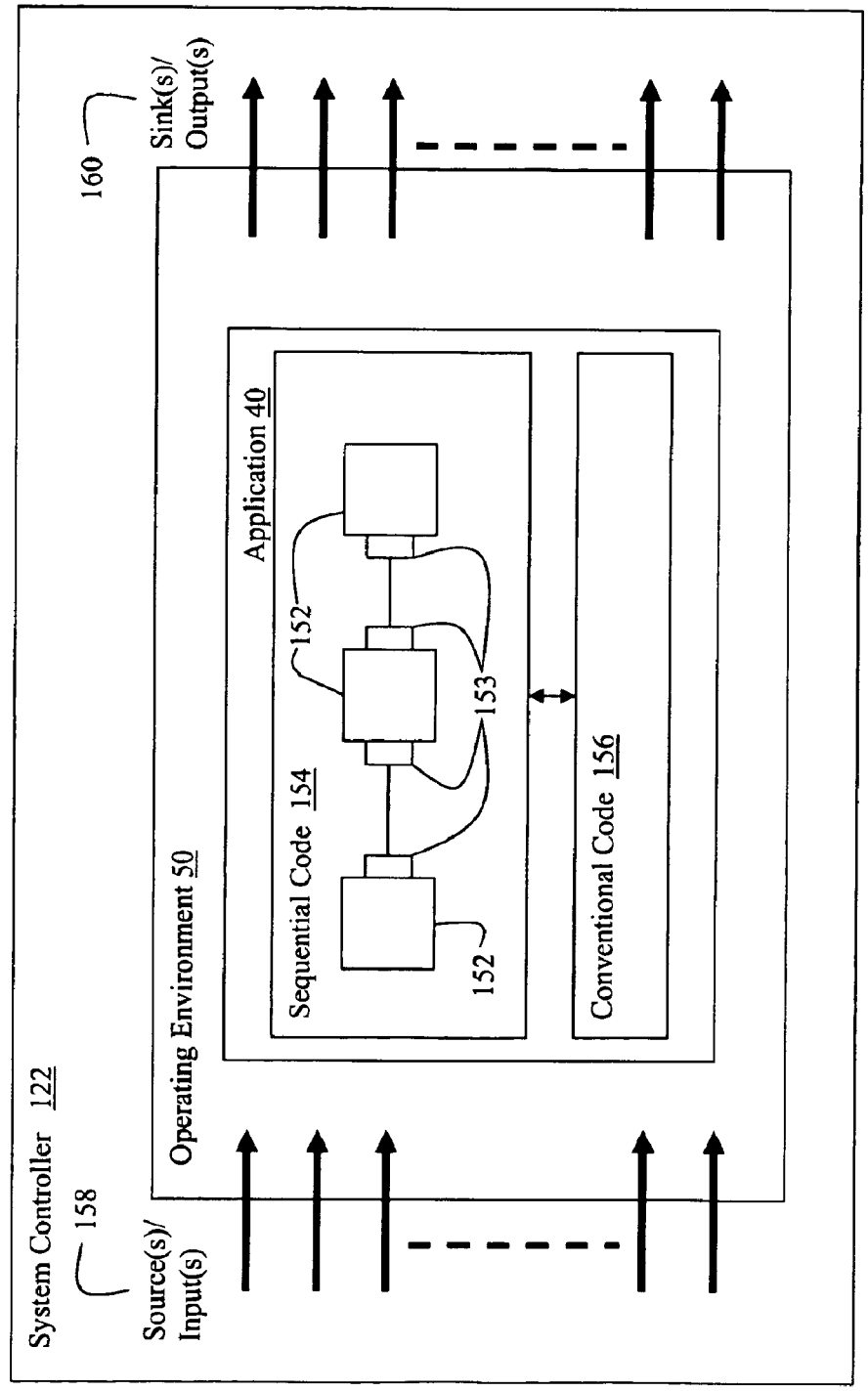
FIG. 6 depicts a logical representation of the system controller of FIG. 5.

FIG. 6 shows the data flow within one embodiment of the system controller 122. The system controller 122 comprises one or more input sources 158 ("inputs"), an operating environment 50, and one or more output sinks 160 ("outputs"). The inputs 158, provide data to the operating environment 50 from the ultrasound system 100. Once this data has been processed by the operating environment 50, it is passed to one or more of the outputs 160. The operating environment 50 comprises a processing environment in which at least one application 40 may execute, and is designed to provide a coupling between the executing applications 40 and the inputs 158 and outputs 160, optionally by using the ultrasound stream manager 30 (not shown in the figure) as described above.

The operating environment 50 may also be configured to receive system configuration information via global variables. Parallel processing, specialized processors (such as DSPs, ASICs and FPGAs), and distributed processing can all be utilized by the operating environment 50. In one embodiment, operating environment 50 allows multiple applications 40 to run in parallel.

As used herein, the terms sequential and incremental are used to refer to applications or computer operating environments/architectures which operate incrementally on data streams, i.e. operate on a portion of the data, or a subset thereof, in the stream as it is received and generating an output, before processing the next data, portion, or subset thereof. Typically, a sequential or incremental application is implemented, as described herein, as a series of processing stages, each stage consuming its input from a source or prior stage and generating an output to a sink or to the next stage before consuming and processing the next input. This is distinguished from the use of the term "sequential" for computer architectures to distinguish these architectures from parallel processing architectures which generally refer to the way in which computer program code is executed by the architecture, both of which may be used to implement the disclosed sequential/incremental processing environment. In the disclosed architecture, multiple streams may be incrementally/sequentially processed, wherein the incremental processing of each stream occurs in parallel with the incremental processing of the other streams.

As will be discussed, the operating environment 50 supports the execution of conventionally written applications 40, sequentially written applications 40 and/or applications 40 written using both sequential and conventional programming code and techniques. Applications 40 receive input data, process that data and generate output data. Conventional application 40 receive all or a portion of the input data and process that data through a collection of interdependent functions and/or procedures and then generate data outputs. Sequential/incremental applications 40 receive the input data in succession, i.e. incrementally, over time and process each input datum as it arrives through a series of independent processing stages, the last stage of which generates the data outputs. A mixed application 40 combines a conventional application 40 with one or more sequential functions or "applets." Although each processing stage must wait for the previous stage to generate its output before processing that output, the processing performed by the particular stage is independent of the other stages, i.e. is self-contained and does not involve the other stage, e.g. the previous stage is free to accept and process additional input. These applets perform specific tasks for the conventional application 40 which are better performed sequentially. For example, processing ultrasound data generated by the acquisition hardware 20 in real time may be better performed by a sequential application 40 or applet which can process the data as it arrives from the acquisition hardware 20 in real time.

Each of the one or more applications 40 comprises sequential program code 154 and/or conventional program code 156. As described above, sequential program code 154 comprises a series of one or more processing stages 152. Each processing stage 152 has at least one input and at least one output. The input of a processing stage 152 is coupled to either a source 158 or another processing stage 152. Each of these stages 152 performs one function on the data provided to it, and then passes the data to either another processing stage 152 or to a data sink 160. Processing stages 152 are interconnected with abstract communication interfaces 153 that facilitate the transmission of data between processing stages 152. Each processing stage 152 may be stateless or stateful as will be described. It will be appreciated that each processing stage may perform more than one function, may operate on more than one piece of data at any given time, and may employ feedback to re-process the output(s) or maintain state. Sequential program code 154 is characterized by the way it handles data. Sequential program code 154 processes, i.e. consumes and delivers, data incrementally. In one embodiment, the sequential program code 154 is adapted to interact with conventional program code 156.

Conventional program code 156 is also characterized by the way it handles data. Conventional program code 156 consumes substantially all of its input before producing any output. The data processed by conventional program code 156 can then be forwarded to a sink 162 or back to the sequential program code 154. It should be apparent to one skilled in the art that the logical interconnection between the conventional program code 156 and the sequential program code 154 is implementation and application specific, e.g. the data provided to conventional program code 156 can be taken from any processing stage 152, and can be sent back to the sequential program code segment 154 at any processing stage 152. Alternatively, any function performed by conventional program code 156 can be performed by processing stages 152. In one embodiment of the present invention, sequential program code 154 is implemented using a pipes and filters framework, as described below. It will be appreciated that for a given application 40, there may be more than one conventional code segment 156 and/or more than one sequential code segment 154 and further that multiple applications 40 may share sequential or conventional program code segments 154 and 156.

A pipes and filters framework, also referred to herein as an architecture, divides the task of a system, i.e. an application program, into several sequential processing stages. It will be appreciated that a pipes and filters architecture defines a logical structure for application development and implementation as well as a logical environment in which applications so constructed may be executed. It will be further appreciated that the underlying physical implementation of the pipes and filters architecture may depend on the underlying hardware and programming environment on top of which the pipes and filters architecture is implemented and all such physical implementations and programming environments are contemplated, including the ultrasound system described herein. These stages are, in one sense, logically coupled with each other by the data flow through the system—the output of one stage is the input to the subsequent stage.

Each processing stage is implemented by a "filter" component. A filter consumes and delivers data incrementally, in contrast to consuming all of its input before producing any output, to achieve low latency and enable real parallel processing. The input of the system is a data source, such as the ultrasound transducer or a stored file. The output flows into a data sink such as a file, terminal, animation program and so on. Data source filters and data sink filters are abstractions of the actual data sources and data sinks of the system. All filters are logically interconnected by "pins." Pins facilitate the flow of data between adjacent processing stages. A sequence of interconnected processing filters between a data source filter and data sink filter is referred to as a processing pipeline or pipeline. A pipeline may optionally contain "pipes" and "allocators." As will be described below, data source filters, data sink filters, processing filters, pipes, pins and allocators are logical programmatic constructs which are abstractions of actual programming code and/or hardware elements of the physical system in which the pipes and filters architecture is implemented. It will be appreciated that each of these constructs may be actually implemented in many different ways depending, as described above, upon the physical implementation and programming environment, and that the functionality of two or more of these constructs may be combined into a single construct or that any one of these constructs may be further logically divided into two or more additional constructs each performing part of the functionality of the larger construct.

A data source filter is a construct which provides data to one or more filters, either through "pins" or a combination of "pins" and "pipes", described in more detail below. In one embodiment, a data source filter may be implemented as a filter whose function is to provide data to the pipeline from a physical data source within the system. Data sources filters are abstractions of actual sources of data, i.e. system outputs, from within the hardware and/or software of the ultrasound system. The pipes and filters architecture manages the actual interface between a particular data source filter and the actual source of data it represents, i.e. provides access to the actual data and allows control over the flow of data. Effectively, a data source filter is a "tap" into a particular point in the ultrasound system 100 from which data may be siphoned and directed to one or more applications 40 with or without affecting the system operation. In one embodiment, an ultrasound stream manager 30 is provided, described in more detail below, which manages the available data sources and data sinks, described below. It should be noted that while the ultrasound stream manager 30 is adapted to manage data sources and data sinks, data source filters and data sink filters can be managed directly by an application 40. Effectively, a data source filter is a standardized Application Programming Interface ("API") to some output point within the ultrasound system. Applications 40 that require data from a particular source within the ultrasound system 100 need only know how to interact with the corresponding data source filter.

Standardization of the data source filter interface permits modularity among applications 40 and sources of data. For example, an application designed to operate on a live data stream from the ultrasound transducer is equally capable of operating on a pre-recorded data stream supplied from a storage device. In this case, the user may choose which data source filter to connect the application to, or the application itself may provide functionality to allow the user to switch among different data source filters. Data source filters may provide inputs, such as flow control inputs which allow applications to control the flow of data from the data source, or other inputs to control other aspects of the data source.

Data sources include live data sources such as the transducer output, stored data sources such as a hard disk, and sources available via a network interface, either wired or wireless, of the ultrasound system 100, such as remote ultrasound systems or remote storage devices. A particular source of data may be shared among multiple applications 40 by creating more than one data source filter associated with the particular source of data. In one embodiment, data sources filters are created on demand, i.e. when an application requests access to a particular source of data. In one embodiment, data sources may be cloned, wherein the cloned data source is copy of the original data source but may not be modified. Exemplary sources of data include both hardware, i.e. physical sources, and software, i.e. logical, sources such as user interface inputs, B-Mode image data, Color Mode image data, BC-Mode image data, Doppler image data, M Mode image data, pre-scan converted data, RF data, IQ data, waveform data such as Doppler derived, ECG/EKG, pulse, respiratory function and other physiological waveforms, phono, auxiliary, audio and video data. B-Mode image data comprises a rectangular array of pixels depicting the intensity of the echo data acquired by the transducer. Color Mode image data displays the velocity and the magnitude of the echo data. In BC-Mode, both the Brightness and Color components are displayed in a single image. Doppler image data comprises frequency analysis of the echo data. M-Mode image data represents a cross-sectional view of a given location being scanned. Pre-scan converted data is the data signal being supplied to the scan converter 112. RF data is the raw echo samples. IQ data is data derived from the RF signal and represents the magnitude and direction of the echo. Waveform data can be any waveform that can be encoded as a pair of coordinates for each column on the display. Typically, waveform data is used to represent ECG/EKG and Doppler derived images. Video data is a digital video sample representative of luminance and chrominance. Audio data is an amplitude representation of an audio signal. The data provided by a particular data source is characterized by various properties. The data may be streaming data, such as a live feed from the transducer, or non-streaming data such as a system control variable or user interface control setting. In one embodiment, streaming data is further characterized by a data format, a frequency or rate, and/or a number of image bytes per sample. As will be described, the data source, via the ultrasound stream manager 30, normalizes the data received from the source of data to a general data format and controls the data flow.

It will be appreciated that the possible sources of data and the number of data source filters associated with the available sources of data is implementation dependent. In one embodiment, the sources of streaming data and the number of data source filters that can be associated with the available sources of the streaming data are limited and fixed by the architecture. In this embodiment, the streaming data sources include 2D image data, trace stream data (Doppler and M-Mode) and waveform data. Up to four data streams may be defined for the 2D data stream, referred to as Streams 0–3. In this embodiment, the video hardware of the ultrasound system is limited to displaying a maximum of four 2D streams acquired at any given time. Up to two data sources may be defined for the trace stream data, referred to as Streams 3 and 4, and up to three data sources may be defined for waveform data, referred to as Streams 5–7. Further, in one embodiment, the trace stream data sources utilize one of the 2D stream data sources such that when using the trace data source only three of the four 2D data sources are available. Further, M-Mode and Doppler cannot be displayed simultaneously. Each waveform data source can acquire up to two waveform data streams.

A data sink is similar to a data source but receives data from one or more filters, either through "pins" or a combination of "pins" and "pipes", described in more detail below. Data sink filters are abstractions of actual inputs to other parts of the hardware and/or software of the ultrasound system 100. The pipes and filters architecture manages the actual interface between a particular data sink filter and the actual system output it represents, i.e. provides access to the output and provides control over the flow of data. Effectively, a data sink is a "tap" into a particular point in the ultrasound system into which data may be introduced by one or more applications 40 with or without affecting general system operation. As will be described below, in one embodiment, the available data sinks are managed by an ultrasound stream manager 30. Effectively, a data sink filter is a standardized API to some output point within the ultrasound system. Applications 40 that need to send data to a particular output within the ultrasound system need only know how to interact with the corresponding data sink filter. As with data sources, standardization of the data sink interface permits modularity among applications 40 and data outputs. For example, an application designed to display data on a video display is equally capable of sending its output to a video recorder. In this case, the user may choose which data sink filter to connect the application to, or the application itself may provide functionality to allow the user to switch among different data sinks via their corresponding filter(s).

Data sinks include live data sinks such as a video display 118 or user interface 120 (graphic user interface or other system indicators), stored data sinks such as a hard disk 242 or video recorder 244 and sinks available via a network interface, either wired or wireless, of the ultrasound system 100, such as remote ultrasound systems, remote terminals, remote displays or remote storage devices. A particular output/sink to the ultrasound system 100 may be shared among multiple applications 40 by creating more than one data sink filter associated with the particular sink. The architecture, via the ultrasound stream manager 30, detects and prevents conflicts among the various applications 40. In one embodiment, data sink filters are created on demand, i.e. when an application 40 requests access to a particular system input. Exemplary system outputs include the ultrasound display 118 via the video controller 116, a video recorder output 244, a remote network device, a memory or processor buffer, a memory or processor register, a printer or a storage device. The data required by a particular system output is characterized by various properties. The output may accept streaming data, such as a processed live feed from the transducer 104, or non-streaming data such as a system control variable or user interface control setting. In one embodiment, streaming data is further characterized by a data format, a frequency or rate, and/or a number of image bytes per sample. As will be described, the data sink filter, or optionally the ultrasound stream manager 30, makes the necessary conversion of the data from the application to the format required by the system input.

It will be appreciated that the possible system outputs and the number of data sink filters associated with the available system outputs is implementation dependent. In one embodiment, the data sinks may include a video displayer filter for rendering video clips, an AVI writer filter for writing compressed clips to disk in the AVI format, a shared memory filter for allowing another process to access the video clip, or a DICOM shared memory filter for allowing another process to access a video clip formatted according to DICOM specifications.

Note that where multiple pipelines are implemented within a single application 40 or among multiple applications 40, a data sink filter may be created for one pipeline which is also the data source filter of another pipeline. In this way, pipelines may be interconnected with the same modularity as described above.

The ultrasound stream manager ("USM") 30 acts as an interface between applications 40 and the actual ultrasound system 100 hardware and/or software. The USM 30 manages the creation and operation of data sources and sinks as described above. In one embodiment, applications 40 register with the USM 30 when they are first executed. The applications 40 then make requests to the USM 30 for the creation of various data sources and data sinks to particular sources of data and system inputs. By registering with the USM 30, the USM 30 need not be pre-configured with knowledge of which applications 40 are present and operating in the system. Registration also permits an application 40 to be part of the ultrasound hardware control sequence. The USM 30 further permits multiple applications 40 to coexist and execute substantially simultaneously and share sources of data and system outputs or sinks. Communication among applications 40 may also be supported.

Further, the USM 30 acts as a control interface for the data sources and sinks, allowing the applications to control the flow of data. Applications 40 use the USM 30 interface to interact with hardware specific sources and sinks. Applications 40 may have on-demand access to data sources or sinks either synchronously or asynchronously. In one embodiment, this access is provided via an Asynchronous Completion Token software design pattern. In one embodiment, a token object is created by USM 30 and passed as part of a notification method invoked upon the arrival of a frame from the acquisition hardware 20. The USM 30 maintains the abstraction of the actual ultrasound system 100 hardware and/or software freeing the applications 40 from the complexities of obtaining inputs and transmitting outputs to the system. As described above, the USM 30 may provide access to any ultrasound specific source of data and any system input within the ultrasound system. Further, the USM 30 may provide normalization and data conversion such that the applications 40 may use a generic data format. The USM 30 normalizes input data from the specific source data format into the generic data format and converts output data from the generic format into a format compatible with the particular system output. For network based data sources or sinks, Quality of Service ("QOS") protocols may be implemented to maintain real-time streaming data flow. For output to a video display, the USM 30 allows the application to specify the display precision, such as in terms of the vertical synchronization signal of the video display hardware. In the case of displaying concurrent data streams on the video display, the USM 30 synchronizes the concurrent streams, allowing them to share the display in multiple windows wherein each display of each data stream is synchronous with the others.

The USM 30 further implements data stream management features to handle high bandwidth data streams, i.e. large and/or fast data streams. In particular, for applications 40 which are unable to process data streams at their native rate, either because the rate is too fast or the application 40 is slowed by competition for system resources, the USM 30 implements a store and notify function to permit the application 40 to catch up once additional system resources become available. Further, in one embodiment, the USM 30 may buffer data streams using two or more fixed capacity buffers which alternate between buffering the data stream and providing the data stream to the applications 40. The alternating "ping pong" approach enables handling of large/long data streams that would otherwise exceed the capacity of a single buffer. In particular, this enables use of the ultrasound system as a playback device for pre-recorded data streams.

Referring back to the pipes and filers architecture, filter components, or filters, are the processing stages of the pipeline, which process data incrementally. A filter is an encapsulated processing step, stage or function. Filters may have the ability to maintain state or operate statelessly. Filters can be source filters, which generate data, transform filters, which manipulate or transform data, e.g. convert between semantically equivalent format/data representations, or sink filters, which store or render data. Other filter types are also possible, such as an observer filter that monitors pipeline data and notifies client software when a data item of interest is being processed. The function implemented by a filter may generate data samples or provide data samples from the ultrasound system (source filter), transform data samples (transform filter), or sort, render or otherwise output samples (sink filter). Other filters coupled between the source and sink filters receive one or more inputs from data source filters, described above, or other filters, and generate one or more outputs to other filters or to data sink filters. Filters connect to other pipeline components using pins. Pipeline components include filters and pipes, described below. Filters can be either abstract or concrete. An abstract filter defines the interfaces and common behavior for a group of similar filters, i.e. acts as a template, while a concrete filter is an actual implementation of the specific behavior for a given application or group of applications. Using a filter abstraction enables a filter pipeline to be programmed generically so that filters and pipeline behavior can be changed at runtime because all filters share common connection and control interfaces. A concrete filter implements the function for the filter as described above.

Filters can be characterized as either active or passive. An active filter starts processing on its own as a separate process or thread. Active filters may be triggered by the availability of data, the demand for data by a subsequent filter, or some other event or signal. Passive filters, on the other hand, are activated by being called either directly or indirectly by an upstream filter (push) or a downstream filter (pull). Depending on the classification of the filter, the activity of a filter will be triggered by several events. A passive filter will be activated by the subsequent pipeline element pulling output from the filter or the previous pipeline element pushing new input data to the filter. Active filters pull their input from and push their output down the pipeline.

Functions performed by exemplary filters of one embodiment of the present invention include, but are not limited to, determining end-systolic, end-diastolic, peak-systolic, and peak-diastolic values. Filters can be used to calculate maximum and minimum amplitudes for various streams based on temporal rules, as well as determining other stream characteristics. Filters can combine an ECG stream with a 2D stream to create composite information. Notification filters can also be implemented to monitor either the activity of other filters in, or the data of, the pipeline. Other functions performed by exemplary filters can include video image sourcing, video image compression, video image decompression, AVI format writing, and shared memory sinking.

Pipes may be used to interconnect one filter with another filter, a data source with the first filter(s), and/or the last filter(s) with a data sink. Pipes provide a way to buffer data between threads and processes that are asynchronous. This synchronization is accomplished by implementing a first-in, first-out (FIFO) buffer. Pipes can hold data until a subsequent filter requests it and block previous filters from operating if its buffer is full.

Pipes can be implemented in a variety of ways. Pipes can provide program to program messaging using shared memory. Furthermore, pipes can be designed as message passing buffers. Pipes can be TCP/IP based, and can allow for object to object communication. While all pipes must have at least one input and at least one output, multiple inputs and outputs are also possible. For example, a T pipe, i.e. a pipe with two outputs, can be utilized to send the result of one processing stage to multiple subsequent filters. Reverse-T pipes can likewise be used to synthesize data from multiple filters. Feedback pipes may also be provided to feed data outputs back as inputs to a previous filter.

Pins are abstract connection points between filters or between filters and pipes. Pins are able to negotiate the type of data that will be transferred between filters to make sure adjacent filters in the processing pipeline are compatible. By creating these abstract interfaces, arbitrary filters are able to connect in a safe manner that ensures compatibility and eliminates the physical dependencies between filters. The interfaces provided by the pin elements make filters reusable, enabling an application developer to configure an arbitrary set of filters at run time. Allocators provide physical memory for the filters and pipes to work with. Abstract allocators provide an interface and concrete allocators implement that interface for an application or group of applications.

FIGS. 7A–7D show four exemplary implementations of pipes and filters pipelines. FIGS. 7A–C show examples of pipelines using only filter elements. FIG. 7D shows a pipeline incorporating a buffering pipe 320 to buffer data between filter A 304d and filter B 306d. FIG. 7A shows on example of a push pipeline using an active data source filter. In this pipeline, the active data source filter 302a begins the pipeline activity by pushing data 314a to, i.e. transfers data 314a using a push function that indirectly (through pin elements (not shown)) transfers the data to and calls the function associated with, a passive transform filter A 304a. Once the data 314a is received by transform filter A 304a, it performs the function f1 310a on the data and pushes the new data 316a to transform filter B 306a. Transform filter B 306a, also a passive filter, performs the function f2 312a on the data 316a it receives from transform filter A 304a, and pushes the new data 318a to the passive data sink filter 308a, completing the pipeline.

FIG. 7B shows an example of a pull pipeline using an active data sink filter. In this pipeline, the active data sink filter 308b begins the pipeline activity by pulling, i.e. indirectly requesting information and calling another filters' function through a pin, data from the passive transform filter B 306b. Transform filter B 306b, then pulls data from the passive transform filter A 304b, which pulls data from the passive data source filter 302b. This creates cascade of indirect function calls. Data source filter 302b sends data 314b to transform filter A 304b. Transform filter A then performs function f1 310b on the data 314b, creating the new data 316b, which is then passed to transform filter B 306b. Transform filter B 306b then performs function f2 312b on the data 316b, creating the new data 318b. This data 318b is then sent to the data sink filter 308b, completing the pipeline.

FIG. 7C shows an example of a mixed push-pull pipeline. In this pipeline, the active transform filter B 306c begins the pipeline activity by pulling data from the passive transform filter A 304c, which, as described above, in turn pulls data 314c from the passive data source filter 302c. Once the data 314c is obtained by filter A 304c, it performs function f1 310c, creating the new data 316c. This data 316c is then passed to transform filter B 306c. Transform filter B 306c then performs function f2 312c on the data 316c, creating new data 318c. This data 318c is then pushed to the passive data sink filter 308c, completing the pipeline.

FIG. 7D shows an example of a mixed push-pull pipeline using multiple active filters, transform filter A 304d and transform filter B 306d, and a buffering pipe 320. It should be noted that this type of pipeline is most typical. In this pipeline, transform filter B 306d tries to get new data by reading the buffering pipe 320. Because no data has been sent to the pipe at this time, it is empty. The request is thus suspended. Transform filter A 304d, in the meantime, pulls data 314d from the data source filter 302d and performs function f1 310d. Transform filter A 304d then pushes the created data 316d to the buffering pipe 320. Because new data is now available in the buffering pipe 320, transform filter B 306d can continue. The buffering pipe 320 passes the buffered data 328 to transform filter B 306d. Transform filter B 306d then performs function f2 312d, creating the new data 318d, which it pushes to the data sink filter 308d. In parallel with this activity, transform filter A 304d request another block of data 324 from the data source filter 302d. Transform filter A 304d then performs function f1 310d on the new data 324 and tries to push the result, data 326, to the buffering pipe 320. This attempt is blocked if the buffering pipe 320 is full and is allowed if buffering pipe 320 is not full. Once transform filter B 306d finishes pushing data 318d to the data sink filter 308d, it sends another pull request to buffering pipe 320. Depending on the previous condition of the buffering pipe 320, filter A's 304d attempt to push data 326 was either originally allowed or is now allowed as transform filter B 306d created space in the buffer. The new data 326 now gets pushed to the buffering pipe 320, where it is passed along to transform filter B 306d.

While FIGS. 7A–D provide some basic examples of pipelines and their behaviors, it should be apparent to one skilled in the art that many alternate pipeline configurations are possible for use in a diagnostic medical ultrasound system according to the disclosed embodiments. Various pipelines may include any combination of active or passive filters and pipes. The pipeline itself may include feedback loops. Multiple paths can be present in a pipeline through the use of T and reverse-T filters or pipes.

As mentioned above, the acquisition hardware 20 provides a stream of data, representative of the succession of received ultrasonic echoes, for use by an ultrasound streaming application according to one embodiment of the present invention. Alternatively, data can be introduced into an ultrasound streaming application, or sourced, from storage devices, such as a disk, tape or memory buffer. Alternatively data may be sourced from a network device. Furthermore, the data provided by acquisition hardware 20 can represent any ultrasound data. Examples included, but are not limited to, B-mode, C-mode, BC-mode, Doppler, M-mode, pre-scan converted, RF and IQ data. The data can also be representative of waveforms such as ECG/EKG, pulse, respiratory functions, phone, audio, video and auxiliary data.

An application 40 is a software program designed to implement one or more tasks in the ultrasound system 100. Applications 40 may include either sequential or conventional code, or combinations thereof. The sequential code 152 is preferably structured in accordance with the pipes and filters architecture described herein and, as will be described below, the pipe and filters architecture provides a development and execution environment in which such code can easily be developed and implemented. In this regard, a typical application 40 includes at least one pipeline comprising one or more filters and pins, and optionally pipes and allocators. Data is streamed from a data source, processed by the filter elements of the pipeline and streamed to a data sink to implement the given task of the particular application 40. In applications 40 which utilize both conventional and sequential code, the sequential code may be contained within sub-applications or "applets" which are utilized by the conventional code for specific processing tasks such as processing streaming data in real time. Outputs of the applets may be fed back to the conventional code and/or sent directly to a data sink. Applets may operate asynchronously from the conventional code and from other applets. The application 40 may utilize multiple sequential code applets operating concurrently wherein, optionally, the conventional code is used to facilitate communications between applets. In one embodiment, the pipes and filters operating environment provides a library of applets which may be utilized by any application 40. Further, in another embodiment, applets are created from the applet library at the time of invocation, thereby allowing multiple instantiations of the same applet by one or more applications 40.

As discussed above, the USM 30 of the disclosed embodiments provides stream arbitration services capable of being called on by one or more applications 40 concurrently. These services abstract and provide applications 40 access to the ultrasound system 100 to receive streaming data, system configuration parameters and/or user interface input and to output data back to the ultrasound system 100 to be used to control the system 100, presented to the user and/or stored. These services can be used to manage all data inputs and outputs, regulate data flow either autonomously or under application 40 control, and normalize and de-normalize input and output data formats. The USM 30 is designed to transparently optimize the execution of applications 40, such as by taking advantage of system hardware such as specialized co-processors (floating point processors, digital signal processors, etc.), parallel or multithreaded processing functionality. The USM 30 further decouples the applications 40 from the ultrasound system outputs and system inputs, thereby increasing the flexibility of the applications 40 to work with different inputs and outputs, as described above, without recoding or recompiling the application 40. When interacting with multiple applications 40, the USM 30 ensures that each application is allocated appropriate resources and that resource contention is managed.

Further, the disclosed operating environment provides for robust error handling, maintaining data integrity, isolating and reporting errors and preventing errors in one application from corrupting other applications 40 currently executing. In one embodiment, an error logger thread is registered with each buffered pipe and filter which detects errors and places an error object corresponding to the type of error observed in an error handling queue. Each error object includes meta-data that describes the error and the state of the filter/pipe. A dedicated error handler thread processes errors in the error handling queue and takes appropriate action depending on the severity of the error. In one embodiment, the error logger and the error handler are allowed to operate in different threads to avoid thread deadlock issues. Deadlock issues can occur when the error handler determines that the best course of action is to shutdown an entire pipeline and discard any data in the pipeline at the time the error occurred. If the pipeline contains any active filters that operate in their own thread, shutdown of the thread is non-trivial unless the error handling resides in a separate thread context. In another embodiment, the environment may provide for redundant operation to protect mission critical applications.

Other features of the pipes and filters architecture environment include allowing the recombination and reuse of defined filters and pipes as well as allowing filters to be dynamically modified or swapped in and out at run time. The environment further permits the sharing of state information between filters and between applications 40. In one embodiment, a symbol table is provided for allowing filters to store and maintain state for themselves or for an application 40. In managing the data inputs and outputs, the USM 30 permits applications 40 to request dedicated access to specific data streams and modify the properties of those data streams. In embodiments wherein the number of data streams is limited, the environment provides functionality to allow applications 40 to release data streams no longer needed and reallocate those data streams to other applications 40.

Given the decoupled nature of the pipes and filters architecture environment, a development environment may also be provided for facilitating the development of streaming applications 40. In one embodiment, this development environment permits the development, simulation and testing of applications 40 with synthetic inputs and outputs, such as media samples. This permits a developer to easily verify the operation of an application or set of applications in an environment which closely approximates the actual ultrasound system. Individual filters or pipelines, or portions thereof, can be tested in isolation prior to being incorporated into larger pipelines or applications 40. Further, the development environment may provide a library of filters, pipelines or applets which can be replicated, recombined, reused or shared among multiple pipelines or applications 40. In one embodiment, the development environment permits the development of applications 40 using standard object oriented programming techniques, the library providing abstract and concrete classes of filters, pipes, pins, media samples and allocators. The library may also provide standardized data transport protocols for pins, pipes and media samples as well as ultrasound specific data types/structures. Further, the development environment provides for separate compilation of the application components, allowing modification to portions of an application 40 without having to recompile the entire application 40. In one embodiment, the development environment includes a graphic user interface ("GUI"). The GUI displays graphic representations of the application 40 and/or pipelines, such as by using a "filter graph" making it easier for the developer to construct the application. In an alternate embodiment, the development environment is capable of operating on an ultrasound system or a conventional computer system.

Figure 8:
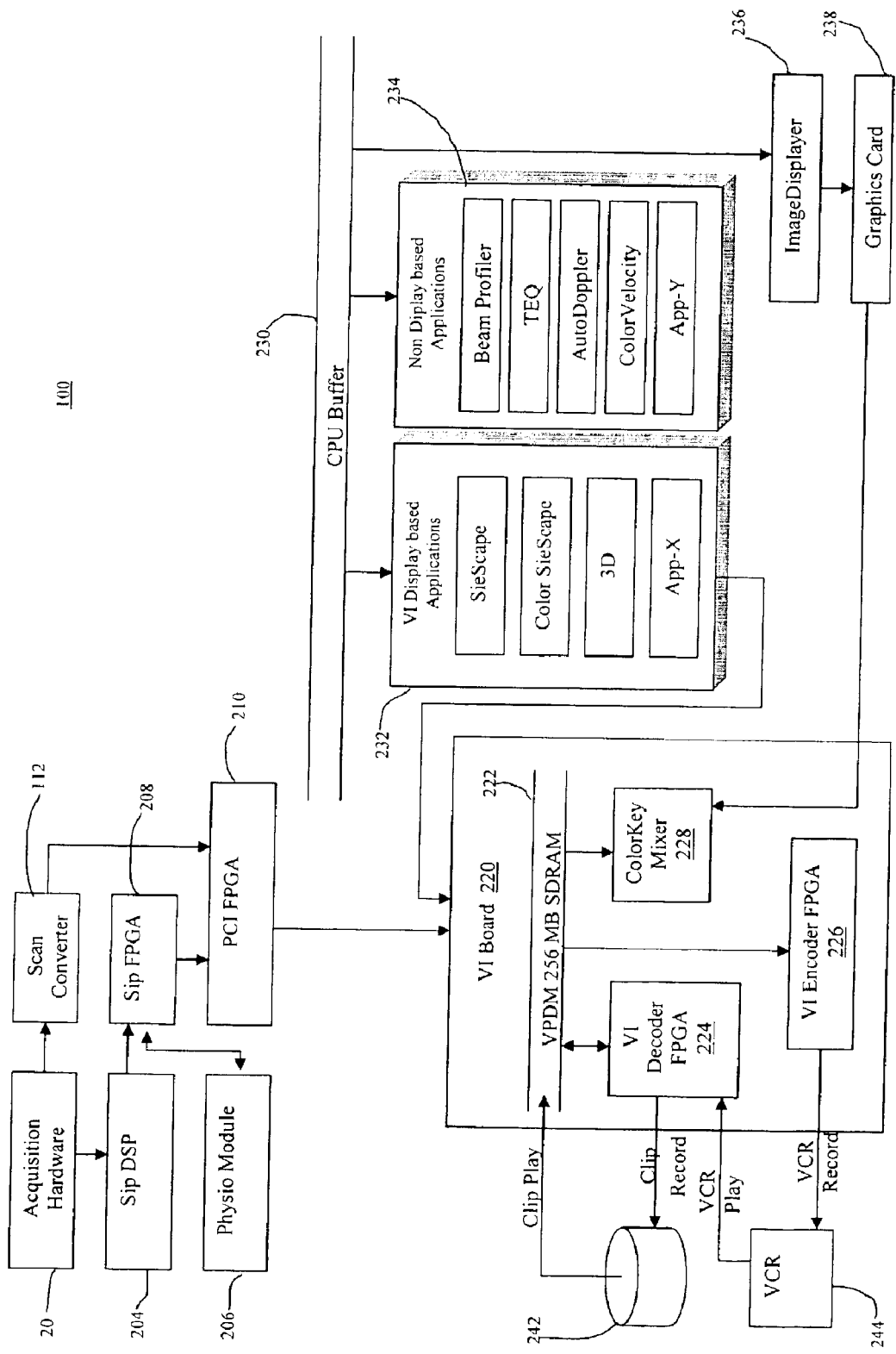
FIG. 8 depicts an alternate block diagram of the diagnostic medical ultrasound system of FIG. 3.

FIG. 8 shows one embodiment of a diagnostic medical ultrasound system 100 featuring a pipes and filters architecture as described above. In this embodiment, the system 100 comprises acquisition hardware 20, a scan converter 112, a single in-line package ("sip") digital signal processor ("DSP") 204, a physio module 206, a single in-line package field programmable gate array ("sip FPGA") 208, a peripheral component interconnect ("PCI") field programmable gate array ("FPGA") 210, a Video Interface ("VI") board 220, a central processing unit ("CPU") buffer 230, display based applications 232, non-display based applications 234, an image displayer 236, a graphics card 238, a video cassette recorder ("VCR") 244 and a magnetic disk 242. The information generated by the acquisition hardware 20 is provided to the scan converter 112 and to the sip DSP 204. In one embodiment, the sip DSP 204 is a single in-line digital signal processor used to generate trace and waveform data for display or acquisition. The physio module 206, used to acquire specified waveform signals, also provides information to the sip DSP 204. The sip DSP 204, in turn, provides information to the sip FPGA 208. The sip FPGA 208 receives the data from the physio module 206 transfers it to the sip DSP 204. The sip FPGA 208 is also connected to the PCI FPGA 210, to which the sip FPGA 208 sends trace or waveform frames received from the sip DSP 204. The PCI FPGA 210 is a field programmable gate array acting as a peripheral component interconnect board, as known in the art. Thus, the PCI FPGA 210 is able to make the information provided to it by the sip FPGA 208 and scan converter 112 available to both VI board 220 and CPU buffer 230.

The CPU buffer 230 of the system controller 122 can be any type of buffer known in the art, including static or dynamic memory. A wide variety of applications have access to the CPU buffer 230. These applications can be characterized as either display based applications 232 or non-display based applications 234. Display based applications 232 create data to be displayed or stored by the ultrasound system via the VI board 220. These applications can include but are not limited to panoramic imaging, 3D imaging, or color imaging. Non-display based applications 234 do not send their results to the display via the VI board 220. Typical applications can include a beam profiler, a TEQ equalizer, Doppler analysis, etc. Although the information generated by non-display based applications 234 is not forwarded to the display via VI Board 220, this information can be used by display based applications 232.

The VI board 220 comprises an application specific integrated circuit (ASIC) VPDM 222, or video processor display manager, two field programmable gate arrays, the VI decoder FPGA 224 and the VI encoder FPGA 226, and a ColorKey mixer 228. In one embodiment, the VPDM 222 comprises 256 megabytes of synchronous dynamic random access memory, or SDRAM. The VPDM 222 (Video Processor Display Manager) ASIC enables the display of overlay and the ultrasound images on the screen by using the color key from the video card output and the data from the Backend hardware subsystem 24 or the stream manager's 30 display stream. In alternate embodiments, the VPDM 222 can comprise various amounts of various types of memories known in the art. The encoder FPGA 226 primarily sends a video composite signal to the VCR 244 for recording. The decoder FPGA 224 assists in getting a signal from the VCR 244 to the VI board 220 for display purposes, and also assists in recording clips to the magnetic disk 242. The ColorKey mixer 228 is used to incorporate color into the display images, as is well known in the art. The ColorKey mixer 228 synthesizes data from the VPDM 222 as well as information from the graphics card 238. The graphics card 238 takes information passed from the CPU buffer 230 to the image displayer 236 and processes the data for use by the VI board 220. The graphics card 238 can be a standard graphics card as is known in the art, such as a Matrox Millenium G400 with 32MB of RAM, an ASUS V7100 2VID with 32 MB of RAM or a LeadTek TI-4200 with 128MB of RAM.

Figure 9:
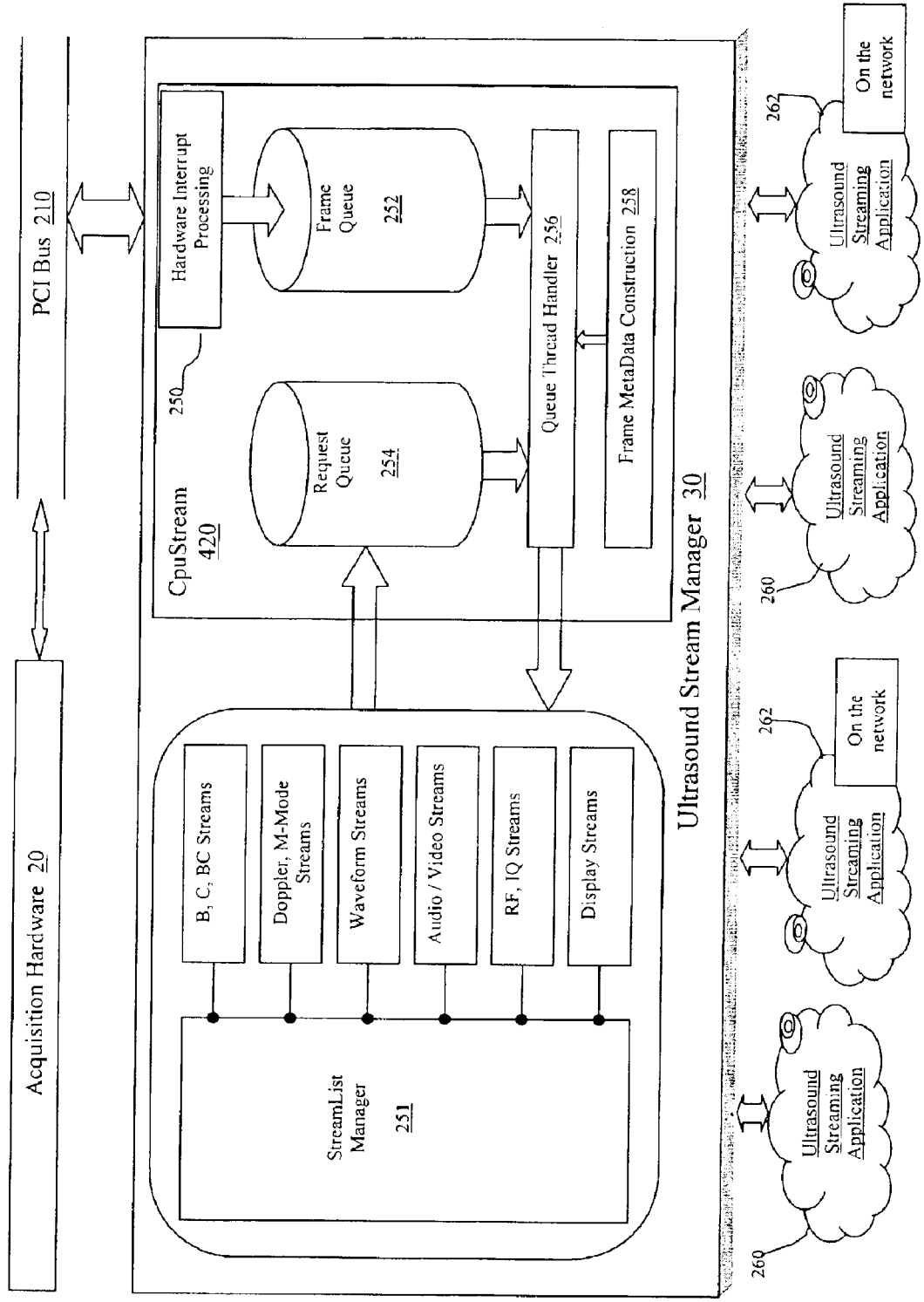
FIG. 9 depicts a block diagram of one embodiment of an ultrasound stream manager for use with the diagnostic medical ultrasound system of FIG. 3.

FIG. 9 shows a more detailed diagram of one embodiment of the ultrasound stream manager 30 for use with a diagnostic medical ultrasound system 100 as described. The system 100 comprises acquisition hardware 20, a PCI bus 210, an ultrasound stream manager 30 as well as various ultrasound streaming applications 260. Further, as shown, various ultrasound streaming applications are also coupled with the ultrasound stream manager via a network 262. In one embodiment, acquisition hardware 20 acquires data representative of received ultrasonic echoes, and transfers this information to the PCI bus 210. As is known in the art, the PCI bus 210 operates to make the information accessible to the processor 128 of the system controller 122 of the diagnostic medical ultrasound system 100. Alternatively, the PCI bus 210 could be configured to operate under any type of bus interface protocol known in the art.

In one embodiment of the present invention, the ultrasound stream manager 30 comprises a CpuStream object 420 and a StreamList Manager 251. In this embodiment, the ultrasound stream manager 30 creates a programmatic construct CpuStream 420 for each stream of the system 100. Each CpuStream object 420 contains a hardware processing interrupt 250, a frame queue 252, a request queue 254, a queue thread handler 256, and a frame metadata construction component 258. The two queues, request queue 254 and frame queue 252, are first-in, first-out (FIFO) circular queues. In one embodiment, the queues comprise a physically contiguous non-paged memory. The StreamList manager 251 is coupled to each CpuStream instance and the various applications 260 and acts as an interface between the two. When an ultrasound streaming application 260 registers with the ultrasound stream manager 30, it will request access to a stream by its number as described above. This request can be synchronous or asynchronous.

When data arrives from the acquisition hardware 20, the hardware interrupt processing 250 adds the data to the frame queue 252 in the form of a programmatic construct FrameInfo (not shown). This construct contains meta-data associated with an incoming frame. In one embodiment, this construct contains offset, timestamp and cine address information for the data being acquired. The timestamp denotes the time the acquisition hardware 20 acquires the information, the cine address denotes the address of the frame in the pre-scan converted buffer, and the offset denotes the offset of the frame in relation to the beginning of the pre-scan converted buffer. As requests from the request queue 254 are serviced, entries in the frame queue 252 are removed. The entry could also be removed from the frame queue 252 if buffer overrun occurs.

The ultrasound stream manager 30 also has a queue thread handler 256 running for each CpuStream object 420 to service the asynchronous requests and to process pending synchronous requests. The queue thread handler 256 is activated when a new request is added to the request queue 254, or when data is added to the frame queue 252 via the PCI bus 210. The queue thread handler 256 will also notify the appropriate application, provided a request is pending in the request queue 254, when either a new frame is added to or there are unread frames in the frame queue 252. Frame MetaData Construction 258 converts the physical address of the frame to a usermode address and incorporates this address as part of the frame meta-data. The usermode address is a virtual address mapped by the ultrasound stream manager 30 to a physical memory address. Frame MetaData Construction 258 also converts the offset and cine address into a physical address and passes this address to the requesting application.

Figure 10A:
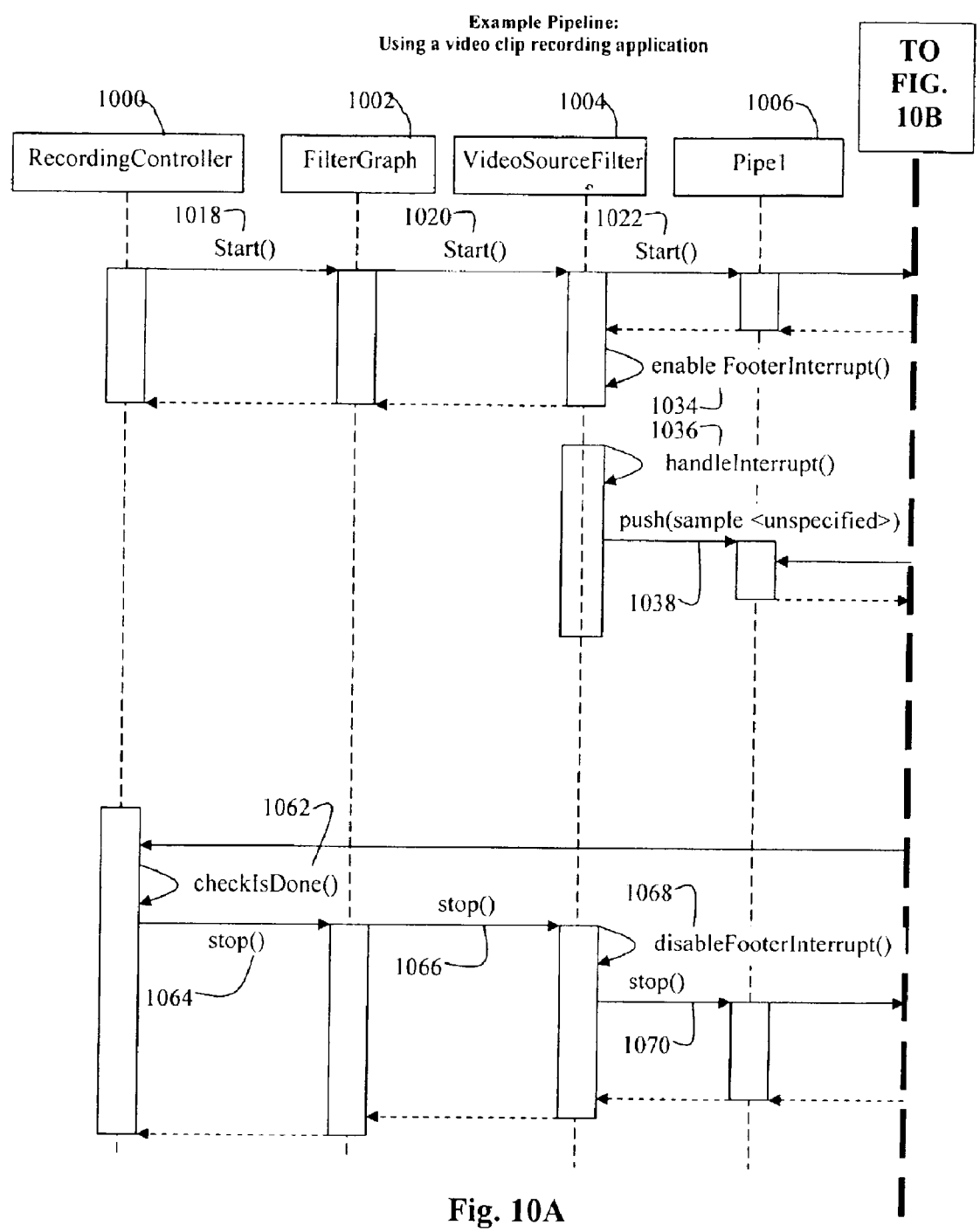
FIG. 10A depicts one half of a representation of one embodiment of the data flow of a pipeline of the diagnostic medical ultrasound system of FIG. 3 incorporating an exemplary clip recording application.
Figure 10B:
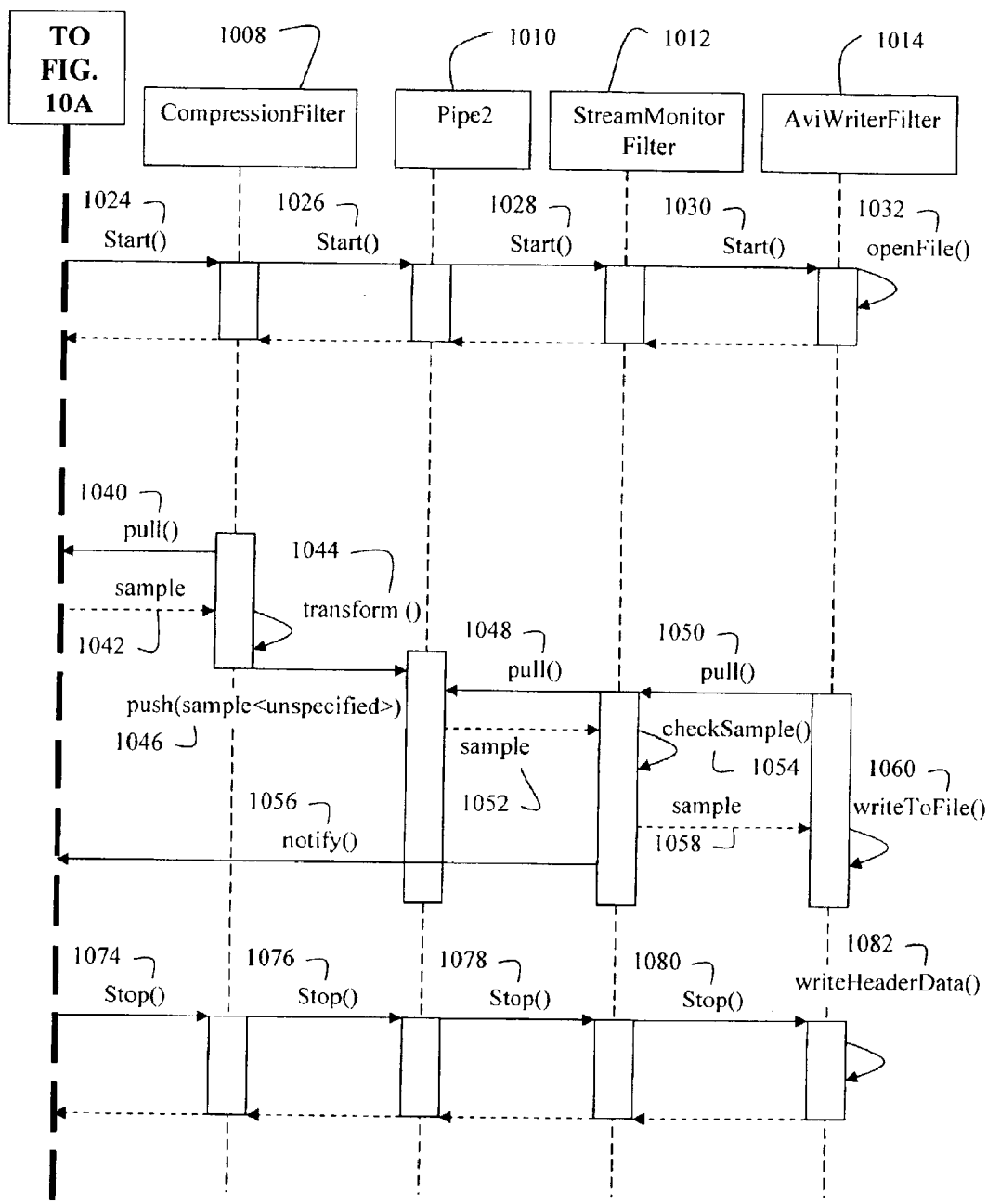
FIG. 10B depicts the other half of a representation of one embodiment of the data flow of a pipeline of the diagnostic medical ultrasound system of FIG. 3 incorporating an exemplary clip recording application.

FIGS. 10A and 10B each show one half of an example of a pipeline of an application interacting with one embodiment of an ultrasound stream manager according to the present invention. Taken together, FIGS. 10A and 10B represent the dataflow of the entire pipeline. It should be noted that all functions calls in the following example are performed indirectly through various pins (not shown). The pipeline represents a clip recording application that can be used to capture a succession of video data frames from the ultrasound display and store them to disk. This image data can be used for diagnosis and can be stored as part of the final exam or study documentation. The pipeline consists of three active filters that operate in their own threads of execution. These are the VideoSourceFilter 1004 which operates primarily in the context of a footer interrupt thread, the Compression Filter 1008 which contains multiple threads for compressing video frames in parallel, and the AviWriterFilter 1014 which writes the frames to a magnetic disk in its own thread.

Initially, the RecordingController 1000 creates the FilterGraph 1002, which manages connection and processing of abstract filter components. All pipeline components share a common abstract API for common operations such as starting, stopping, pausing, resuming, and flushing. Next, the RecordingController 1000 creates each of the pipeline elements including all filters and pipes. The RecordingController 1000 registers a callback with the StreamMonitorFilter 1012 so that it can receive notifications when a desired number of frames has been processed by the pipeline. The RecordingController 1000 calls a method on the FilterGraph 1002 to add the components to the FilterGraph 1002. Components are added in sink first order. As each component is added, the FilterGraph 1002 queries a component's output pins to find a match with its downstream filter's input pins. A match occurs if the filters media types are compatible. If a match is found, a connection is made. If a match is not found, an exception is raised. Once all of the components have been added, the pipeline is ready to capture a video clip.

The RecordingController 1000 calls the start method on the FilterGraph 1002. The FilterGraph 1002 then sends this message to the VideoSourceFilter 1004, which is first filter in the pipeline. The VideoSourceFilter 10004 then propagates this call in a cascading fashion down the pipeline. As each active filter gets the message to start processing samples it activates it internal threads, which immediately start to process data if available. As part of the start method 1024, the CompressionFilter 1008 is initialized and attempts to pull data from Pipe 1 1006 and the AviWriterFilter 1014 opens an output file and attempts to pull 1050 data from Pipe 2 1010 via an indirect call through the StreamMonitor 1012. Finally the VideoSourceFilter 1004 enables the footer interrupt 1034 which starts the process of generating samples.

The ultrasound stream manager 30 provides a frame of data to the VideoSourceFilter 1004 each time the footer interrupt occurs (typically 30 or 60 times per second). The VideoSourceFilter 1004 completely encapsulates interaction with the ultrasound stream manager 30. The footer interrupts facilitate the USM's 30 control over hardware interrupts on demand.

When the footer interrupt occurs, the VideoSourceFilter 1004 takes the sample and calls the push method 1038 on its output pin. Since Pipe 1 1006 is the next component in the pipeline, this effectively puts the sample in a queue. The VideoSourceFilter 1004 will continue to put samples in Pipe 1 1006 asynchronously as provided by the ultrasound stream manager 30. The CompressionFilter 1008 threads pull samples 1042 out of Pipe 1 1006 asynchronously as they become available. The CompressionFilter 1008 compresses the sample 1042 with the transform method 1044 and then pushes 1046 the result onto its output pin, which places it in Pipe 2 1010. The AviWriterFilter 1014 indirectly calls the StreamMonitorFilters 1012 pull method 1048, which forwards this request to Pipe 2 1010. If a sample 1052 is available, it is returned to the AviWriter 1014, which writes the data to the disk file.

For each sample 1052 that is passed down the pipeline, the StreamMonitorFilter 1012 counts the sample 1052 and determines whether it needs to notify the RecordingController 1000 that the desired number of frames has been processed. Once the desired number of frames has been captured, the StreamMonitorFilter 1012 notifies 1056 the RecordingController 1000. The RecordingController 1000 then calls its own internal method, checkIsDone 1062, to verify that the desired number of frames has been captured. If the clip has the desired number of frames, the RecordingController 1000 calls stop 1064 on the FilterGraph 1002, which calls stop on the VideoSourceFilter 1004. The VideoSourceFilter 1004 then disables the footer interrupt 1068, which tells the ultrasound stream manager 30 to stop producing frames. The VideoSourceFilter 1004 then calls stop on downstream filters in a manner very similar to the starting the pipeline. On receiving the stop message, the AviWriterFilter 1014 calls its writeHeader 1082 method to finalize the data and close the file.

Figure 11:
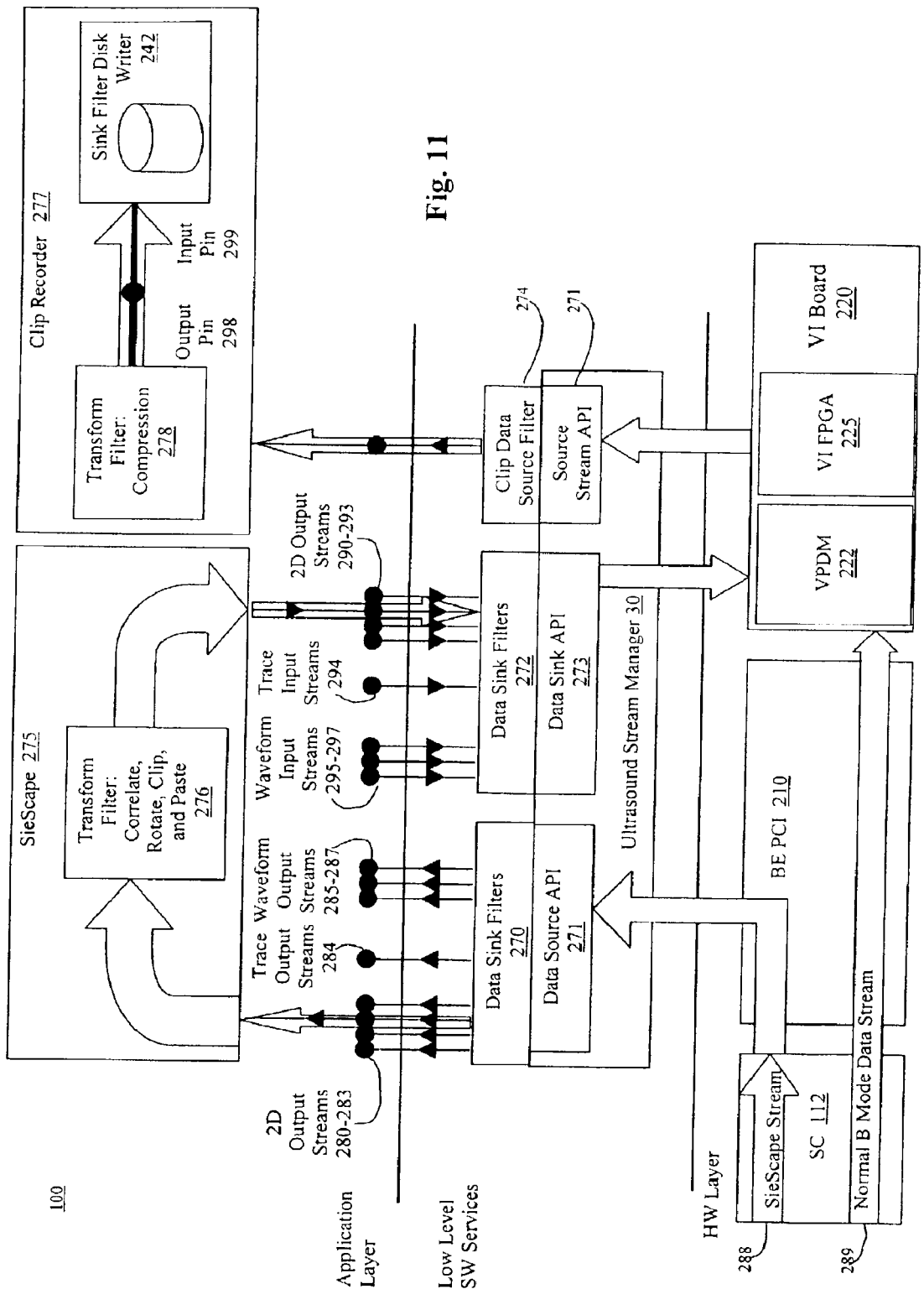
FIG. 11 depicts a second alternate block diagram of the diagnostic medical ultrasound system of FIG. 3.

FIG. 11 shows the data flow of one embodiment of the diagnostic medical ultrasound system of the present invention, using the panoramic imaging application Siescape™ as an exemplary streaming application. Siescape™ permits a clinician to acquire panoramic images in real time simply by activating the function and sliding the transducer along the intended path. In this embodiment, the system comprises a scan converter 112, a BE PCI board 210, an ultrasound stream manager 30, a plurality of output streams 280–287, a plurality of input streams 290–297, a SieScape application 275, a VI Board 220, and a clip recorder application 277.

The scan converter 112 is coupled to the BE PCI board 210 and processes both a Siescape stream 288, a 2D stream, and normal B mode data stream 289. The Siescape stream is passed to the backend PCI bus 210, which makes the data accessible to the ultrasound stream manager 30. The pipes and filters architecture comprises data source filters 270, data sink filters 272, and a clip data source filter 274, which encapsulate the source stream API 271 and sink stream API 273 of the USM 30. The data source filters 270 make the data accessible to the ultrasound streaming application Siescape 275, via the multiple 2D output streams 280–283. As discussed earlier, each of the stream numbers correspond to a particular type of stream. Four output streams 280–283 represent 2D streams. One output stream 284 represents a trace stream. Three output streams 285–287 represent waveform streams. Similarly, ultrasound stream manager 30 has multiple input streams for acquiring data output from the various ultrasound streaming applications employed in a given embodiment. In this embodiment, three input streams 295–7 represent waveform streams, one input stream 294 represents a trace stream, and four input streams 290–93 represent 2D streams.

Initially, the ultrasound streaming application Siescape 275 registers with the ultrasound stream manager 30 and acquires data from the stream. Siescape 275 then performs the various transform filters 276 on the information. Namely, the SieScape application performs a correlate function, a rotate function, a clip function and a paste function. In this embodiment, the functions are performed as a pipeline in a pipes and filters framework. It should be readily apparent to one skilled in the art that these functions could be performed by sequential code segments, as conventional code segments, or as a combination of both. Once the data has been transformed by the SieScape application, the information is sent back to the ultrasound stream manager via a 2D input stream.

Once this information is received by the ultrasound stream manager 30, the information will be forwarded to the VPDM 222 of the VI board 220. In this example, the information is then sent to the clip recorder application 277 by the VI FPGA 225 via the source stream API 275 and clip data source filter 274. The clip recorder application 277 compresses the data with the transform filter 278 and transmits the data to sink filter disk writer 242 via output pin 298 and input pin 299.

Another exemplary application which utilizes the pipes and filters architecture of the disclosed embodiments is an Automated Boundary Detection ("ABD") application. An ABD application identifies the boundaries of an object represented by the ultrasound image data, whether the image data is a live data feed from the transducer or prerecorded. For example, when imaging the heart of a subject, the ABD application can determine the boundaries of the heart, i.e. the locations of the cardiac walls. This is useful, for example, to estimate the cardiac blood volume of the subject heart. Prior ABD applications could only operate on pre-recorded image data, either post scan converted or pre-scan converted, and therefore were incapable of operating in real time.

An ABD application implemented as a streaming application 40 executing on an ultrasound system 100 having the disclosed pipes and filters architecture is capable of processing the live image data stream, either post scan converted or pre-scan converted, in real time, increasing the usefulness of this diagnostic tool.

In operation, the real time ABD application sets up data stream using the ultrasound stream manager 30 by requesting a data source for live B-mode image data, either B-mode or BC-mode, etc. The ABD application further instructs the ultrasound stream manager 30 to simultaneously send the live B-mode image data to the video display. An asynchronous notification handler is then enabled which gives full control of the data stream to the ABD application, as described above. This enables acquisition of the image data on demand. The ABD application then determines the boundary or boundaries of the objects currently being imaged using techniques that are known in the art.

Once the ABD application receives control of the image data stream, the ABD application may control data throughput by slowing or speeding up the acquisition rate, for example, if the clinician changes the rate at which they are moving the transducer over subject. Further, the ABD application may specify a region of interest ("ROI") on the data stream so it can control the amount of data being processed, thereby increasing application performance. In one embodiment, the ABD application may provide control feedback to the user, or directly to the transducer 104, for adjusting the beam steering or beam focus, or other parameters of the image scan, so as to achieve optimal imaging for boundary detection.

It will be appreciated that there are many known ultrasound applications which may be reconfigured to take advantage of the disclosed pipes and filters architecture. Further, applications may be configured to use feedback to automate ultrasound functions, control beam depth, focus or steering, select a region of interest, or manipulate other parameters of the ultrasound system.

A clip playback application allows the user to view previously recorded video clips in order to perform diagnoses or to study ultrasound images. The application consists of a control component, a playback source filter, a decompression filter and a video displayer sink filter (which encapsulates or hides calls to the USM's 30 stream APIs).

It is therefore intended that the foregoing detailed description be regarded as illustrative rather than limiting, and that it be understood that it is the following claims, including all equivalents, that are intended to define the spirit and scope of this invention.

We claim:

1. A component for use with a diagnostic medical ultrasound system comprising:

an input source operative to provide a sequence of digital signals, each of said sequence of digital signals having been derived from at least one ultrasonic echo received by an ultrasound transducer from a subject in response to transmission of acoustic energy into said subject by said transducer;

at least one processor coupled with said input source and comprising an incremental data processing architecture for executing a first application program, said first application program operative to incrementally receive and process each of at least a subset of said sequence of digital signals in succession, said first application program comprising a plurality of processing stages, each of said plurality of processing stages sequentially coupled with another of said plurality of processing stages, each of said plurality of processing stages comprising an input, an output and a function, said input of one of said plurality of processing stages being coupled with at least one of said input source and said output of another of said plurality of processing stages, each of said plurality of processing stages operative to receive data via said input, perform said function and generate a result on said output, wherein said one of said plurality of processing stages coupled with said input source receives each of said subset of said sequence of digital signals in succession; and wherein said output sink is further operative to receive said result from said output of at least one of said plurality of processing stages; and an output sink coupled with said at least one processor and operative to receive said processed digital signals from said first application program.

2. The component of claim 1, wherein said input source comprises: a transducer operative to transmit acoustic energy into a subject and receive a substantially continuous succession of echoes therefrom; and a converter coupled with said transducer and operative to convert each of said substantially continuous succession of received echoes into said sequence of digital signals as said echoes are received by said transducer.

3. The component of claim 1, wherein said input source comprises a data storage device operative to store a representation of said sequence of digital signals previously acquired from an ultrasound transducer, said storage device operative to provide said stored sequence of digital signals to said processor.

4. The component of claim 3, wherein said input source comprises one of a DVD, CD or magneto-optical device.

5. The component of claim 1, wherein said input source is coupled with said processor via a network.

6. The component of claim 1, wherein said input source comprises a second application program different from said first application program and executed by said at least one processor.

7. The component of claim 1, where said input source comprises an ultrasound stream manager.

8. The component of claim 1, wherein said first application programs comprises a plurality of filters, each of said filters interconnected with another of said plurality of filters.

9. The component of claim 8, wherein at least one of said plurality of filters is interconnected with another of said plurality of filters by a pipe.

10. The component of claim 1, wherein each of said plurality of processing stages is caused, by the receipt of said data from said input, to perform said function and generate said result.

11. The component of claim 1, wherein each of said plurality of processing stages operates independent of the other said plurality of processing stages.

12. The component of claim 1, wherein said function comprises a manipulation of said data, said result comprising said manipulated data.

13. The diagnostic medical ultrasound system of claim 1, wherein said function comprises a transformation of said data, said result comprising said transformed data.

14. The component of claim 1, wherein said processor provides an interface between at least one of said plurality of processing stages and said input source and said output sink such that said at least one of said plurality of processing stages may receive said digital signal from said input source and transmit said result to said output device.

15. The component of claim 1, wherein said first application program comprises an algorithm, said algorithm comprising multiple processing steps, wherein each of said plurality of processing stages comprises at least one of said processing steps.

16. The component of claim 1, wherein said plurality of processing stages comprises a pipeline.

17. The component of claim 1, wherein each of said plurality of processing stages processes one of said sequence of digital signals prior to processing another of said sequence of digital signals.

18. The component of claim 1, wherein said output sink comprises a display operative to visually present said received result to a user of said system.

19. The component of claim 1, wherein said output sink comprises a storage device.

20. The component of claim 1, wherein said output sink comprises a second application program different from said first application program and executed by said at least one processor.

21. The component of claim 1, where said output sink comprises an ultrasound stream manager.

22. A method of operating a diagnostic medical ultrasound system comprising:

(a) receiving a sequence of digital signals by an input source, each of said sequence of digital signals having been derived from an ultrasonic echo received by an ultrasound transducer from a subject in response to transmission of acoustic energy into said subject by said transducer;

(b) executing a first application program on at least one processor coupled with said input source, said at least one processor comprising an incremental data processing architecture;

(c) receiving and processing incrementally, by said first application program, each of at least a subset of said sequence of digital signals in succession;

(d) transmitting said processed digital signals from said first application to an output sink coupled with said at least one processor;

(e) providing, by said first application program, a plurality of processing stages, each of said plurality of processing stages sequentially coupled with another of said plurality of processing stages wherein each of said plurality of processing stages comprises an input, an output and a function, said input of one of said plurality of processing stages being coupled with at least one of said input source and said output of another of said plurality of processing stages, (f) receiving data by each of said plurality of processing stages via said input;

(g) receiving, by said one of said plurality of processing stages coupled with said input source, a subset of said sequence of digital signals in succession;

(h) performing said function;

(i) generating a result on said output; and (j) transmitting, to said output sink, said result from said output of at least one of said plurality of processing stages.

23. The method of claim 22, wherein (a) further comprises using a transducer to transmit acoustic energy into a subject and receive a substantially continuous succession of echoes therefrom, converting each of said substantially continuous succession of received echoes into said sequence of digital signals as said echoes are received by said transducer.

24. The method of claim 22, wherein (a) further comprises storing, in a storage device, a representation of said sequence of digital signals previously obtained from an ultrasound transducer and providing said sequence of digital signals from said storage device.

25. The method of claim 22, wherein (a) further comprises receiving said subset of said sequence of digital signals from a second application program different from said first application program executing on said at least one processor.

26. The method of claim 22, wherein (a) further comprises receiving said subset of said sequence of digital signals from an ultrasound stream manager.

27. The method of claim 22, wherein (d) further comprises visually presenting said received result to a user of said system.

28. The method of claim 22, wherein (d) further comprises storing said received result in a storage device.

29. A diagnostic medical ultrasound system comprising:

input source means for providing a sequence of digital signals, each of said sequence of digital signals having been derived from an ultrasonic echo received by an ultrasound transducer from a subject in response to transmission of acoustic energy into said subject by said transducer;

processor means coupled with said input source and comprising an incremental data processing architecture means for executing at least one application program means for receiving and processing a subset of said sequence of digital signals in succession; and output sink means coupled with said processor for receiving said processed subset of said sequence of digital signals from said at least one application program means; and wherein, said at least one application program means comprises a plurality of processing stage means, each of said plurality of processing stage means sequentially coupled with another of said plurality of processing stage means, each of said plurality of processing stage means comprises an input means, an output means and a function means, said input means of one of said plurality of processing stage means being coupled with at least one of said input source and said output means of another of said plurality of processing stage means, each of said plurality of processing state means operative to receive data via said input means, perform said function means and generate a result on said output means, wherein said one of said plurality of processing stage means coupled with said input source receives each of said subset of said sequence of digital signals in succession; and wherein said output sink means is further operative to receive said result from said output means of at least one of said plurality of processing stage means.

30. A component of a diagnostic medical ultrasound system comprising:

an input source filter operative to incrementally provide a first sequence of digital signals, said first sequence of digital signals having been derived from at least one ultrasonic echo received by an ultrasound transducer from a subject in response to transmission of acoustic energy into said subject by said transducer;

an output sink filter operative to accept a second sequence of digital signals; and a processing filter dynamically coupled with at least one of said input source filter and said output sink filter at a time of execution of said processing filter, said processing filter operative to receive and process each of said first sequence of digital signals in succession, said processing filter comprising a plurality of processing stages, each of said plurality of processing stages sequentially coupled with another of said plurality of processing stages, each of said plurality of processing stages comprises an input, an output and a function, said input of one of said plurality of processing stages being coupled with at least one of said input source and said output of another of said plurality of processing stages, each of said plurality of processing stages operative to receive data via said input, perform said function and generate a result on said output, wherein said one of said plurality of processing stages coupled with said input source receives each of said subset of said sequence of digital signals in succession; and wherein said output sink is further operative to receive said result from said output of at least one of said plurality of processing stages.

* * * * *